US012614640B2

(12) United States Patent
Kyyrö et al.

(10) Patent No.: US 12,614,640 B2
(45) Date of Patent: *Apr. 28, 2026

(54) METHOD AND SYSTEM FOR SUPPLEMENTAL SLEEP DETECTION

(71) Applicant: Oura Health Oy, Oulu (FI)

(72) Inventors: Mats Kyyrö, Oulu (FI); Hannu Kinnunen, Oulu (FI); Mari Karsikas, Oulu (FI); Heli Koskimäki, Oulu (FI); Harri Laakkonen, Oulu (FI); Tomi Liiten, Oulu (FI); Johanna Still, Oulu (FI); Kaisa Tarvainen, Oulu (FI); Petteri Lajunen, Oulu (FI); Matias Kukka, Oulu (FI)

(73) Assignee: Oura Health Oy, Oulu (FI)

( * ) Notice: Subject to any disclaimer, the term of this patent is extended or adjusted under 35 U.S.C. 154(b) by 6 days.

This patent is subject to a terminal disclaimer.

(21) Appl. No.: 18/933,967

(22) Filed: Oct. 31, 2024

(65) Prior Publication Data

US 2025/0062033 A1    Feb. 20, 2025

Related U.S. Application Data

(63) Continuation of application No. 17/729,557, filed on Apr. 26, 2022, now Pat. No. 12,165,771.

(60) Provisional application No. 63/180,381, filed on Apr. 27, 2021.

(51) Int. Cl.
*G16H 50/30* (2018.01)
(52) U.S. Cl.
CPC .................................. *G16H 50/30* (2018.01)

(58) Field of Classification Search
CPC ...................................................... G16H 50/30
See application file for complete search history.

(56) References Cited

U.S. PATENT DOCUMENTS

| | | | | | |
|---|---|---|---|---|---|
| 2,753,435 | A | * | 7/1956 | Jepson | H05B 1/0272 126/210 |
| 4,132,262 | A | * | 1/1979 | Wibell | F25D 17/02 165/206 |
| 4,459,468 | A | * | 7/1984 | Bailey | G05D 23/1919 607/104 |
| 4,777,802 | A | * | 10/1988 | Feher | A47G 9/0215 5/482 |
| 4,858,609 | A | * | 8/1989 | Cole | A61M 21/00 600/26 |

(Continued)

*Primary Examiner* — Michael I Ezewoko
(74) *Attorney, Agent, or Firm* — ArentFox Schiff LLP

(57) ABSTRACT

A method and system for supplemental sleep detection is described. A system may receive data associated with a user from a wearable device worn by the user, and may detect a primary sleep period for the user based on the received data. The system may additionally detect a supplemental sleep period including a duration that exceeds a threshold duration based on the received data. In some implementations, the system may cause a graphical user interface (GUI) of a user device to display an indication of the detected supplemental sleep period, and may receive a confirmation of the supplemental sleep period via the user device and in response to the indication of the detected supplemental sleep period. The system may subsequently generate one or more insights associated with the user based on the primary sleep period and the supplemental sleep period and, in some implementations, in response to the confirmation.

18 Claims, 11 Drawing Sheets

(56) References Cited

U.S. PATENT DOCUMENTS

| | | | | | |
|---|---|---|---|---|---|
| 5,033,136 A * | 7/1991 | Elkins | A47C 21/048 | | |
| | | | 5/500 | | |
| 5,304,112 A * | 4/1994 | Mrklas | A61M 21/0094 | | |
| | | | 600/27 | | |
| 5,329,096 A * | 7/1994 | Suematsu | H05B 3/34 | | |
| | | | 219/217 | | |
| 5,448,788 A * | 9/1995 | Wu | A47C 21/048 | | |
| | | | 5/421 | | |
| 5,703,637 A * | 12/1997 | Miyazaki | G02B 27/0172 | | |
| | | | 348/E5.145 | | |
| 5,894,615 A * | 4/1999 | Alexander | A61F 7/00 | | |
| | | | 165/61 | | |
| 5,948,303 A * | 9/1999 | Larson | H05B 3/342 | | |
| | | | 219/486 | | |
| 6,163,781 A * | 12/2000 | Wess, Jr. | G06Q 40/08 | | |
| | | | 715/236 | | |
| 6,163,907 A * | 12/2000 | Larson | A47C 21/048 | | |
| | | | 5/691 | | |
| 6,273,810 B1 * | 8/2001 | Rhodes, Jr. | A47C 7/467 | | |
| | | | 297/452.47 | | |
| 6,371,976 B1 * | 4/2002 | Vrzalik | A61F 7/0097 | | |
| | | | 607/104 | | |
| 6,484,062 B1 * | 11/2002 | Kim | A61M 21/00 | | |
| | | | 600/26 | | |
| 6,581,224 B2 * | 6/2003 | Yoon | F24D 3/16 | | |
| | | | 5/654 | | |
| 6,826,792 B2 * | 12/2004 | Lin | A47C 27/082 | | |
| | | | 219/217 | | |
| 7,041,049 B1 * | 5/2006 | Raniere | A61M 21/02 | | |
| | | | 600/26 | | |
| 7,238,289 B2 * | 7/2007 | Suddath | A61L 9/16 | | |
| | | | 422/186 | | |
| 7,248,915 B2 * | 7/2007 | Ronnholm | A61B 5/4812 | | |
| | | | 600/300 | | |
| 7,306,567 B2 * | 12/2007 | Loree, IV | A61B 5/103 | | |
| | | | 600/595 | | |
| 7,460,899 B2 * | 12/2008 | Almen | A61B 5/02455 | | |
| | | | 600/509 | | |
| 7,524,279 B2 * | 4/2009 | Auphan | G16H 50/30 | | |
| | | | 600/26 | | |
| 7,608,041 B2 * | 10/2009 | Sutton | A61M 21/00 | | |
| | | | 600/300 | | |
| 7,699,785 B2 * | 4/2010 | Nemoto | G08B 21/0461 | | |
| | | | 600/509 | | |
| 7,868,757 B2 * | 1/2011 | Radivojevic | A61B 5/002 | | |
| | | | 340/575 | | |
| 8,096,960 B2 * | 1/2012 | Loree, IV | A61B 5/6828 | | |
| | | | 600/595 | | |
| 8,179,270 B2 * | 5/2012 | Rai | A61B 5/4812 | | |
| | | | 600/300 | | |
| 8,191,187 B2 * | 6/2012 | Brykalski | A61G 7/05769 | | |
| | | | 607/104 | | |
| 8,290,596 B2 * | 10/2012 | Wei | A61N 1/36135 | | |
| | | | 607/45 | | |
| 8,348,840 B2 * | 1/2013 | Heit | G16H 40/67 | | |
| | | | 600/300 | | |
| 8,418,285 B2 * | 4/2013 | Frias | A47C 21/048 | | |
| | | | 5/710 | | |
| 8,529,457 B2 * | 9/2013 | Devot | A61B 5/349 | | |
| | | | 600/536 | | |
| 8,617,044 B2 * | 12/2013 | Pelgrim | A61B 5/165 | | |
| | | | 600/26 | | |
| 8,768,520 B2 * | 7/2014 | Oexman | F24F 11/58 | | |
| | | | 5/421 | | |
| 8,979,730 B2 * | 3/2015 | Naujokat | A61B 5/6804 | | |
| | | | 600/26 | | |
| 9,196,479 B1 * | 11/2015 | Cheng | H10D 62/822 | | |
| 9,720,259 B2 * | 8/2017 | Hart | G02C 7/04 | | |
| 9,727,885 B1 * | 8/2017 | Reier | G16H 40/63 | | |
| 9,999,744 B2 * | 6/2018 | Proud | A61B 5/4842 | | |
| 10,178,972 B2 * | 1/2019 | Raymann | G06Q 10/109 | | |
| 10,379,575 B2 * | 8/2019 | Blum | H04N 23/63 | | |
| 10,795,411 B2 * | 10/2020 | Blum | G02C 7/101 | | |
| 11,347,084 B2 * | 5/2022 | Hart | A61B 3/14 | | |
| 11,694,778 B2 * | 7/2023 | Kaput | G16H 50/70 | | |
| | | | 705/3 | | |
| 11,791,025 B2 * | 10/2023 | Kaput | G16H 10/60 | | |
| | | | 705/3 | | |
| 11,813,076 B2 * | 11/2023 | Youngblood | G16H 40/67 | | |
| 11,822,155 B2 * | 11/2023 | Blum | G02C 7/16 | | |
| 11,880,091 B2 * | 1/2024 | Hart | G02C 7/04 | | |
| 12,165,771 B2 | 12/2024 | Kyyrö et al. | | | |
| 2002/0014951 A1 * | 2/2002 | Kramer | G16H 10/60 | | |
| | | | 340/286.07 | | |
| 2002/0080035 A1 * | 6/2002 | Youdenko | G04B 23/021 | | |
| | | | 340/573.1 | | |
| 2002/0099257 A1 * | 7/2002 | Parker | A61M 21/00 | | |
| | | | 600/27 | | |
| 2002/0124574 A1 * | 9/2002 | Guttman | F25B 21/04 | | |
| | | | 62/3.4 | | |
| 2004/0049132 A1 * | 3/2004 | Barron | A61B 5/0002 | | |
| | | | 600/595 | | |
| 2005/0143617 A1 * | 6/2005 | Auphan | A61B 5/4815 | | |
| | | | 600/26 | | |
| 2005/0154330 A1 * | 7/2005 | Loree | A61B 5/103 | | |
| | | | 600/595 | | |
| 2006/0137099 A1 * | 6/2006 | Feher | A47C 27/082 | | |
| | | | 5/713 | | |
| 2006/0293602 A1 * | 12/2006 | Clark | A61M 21/00 | | |
| | | | 600/300 | | |
| 2006/0293608 A1 * | 12/2006 | Rothman | A61M 21/00 | | |
| | | | 368/9 | | |
| 2008/0046916 A1 * | 2/2008 | Shivaji-Rao | H04N 7/17318 | | |
| | | | 725/112 | | |
| 2008/0221416 A1 * | 9/2008 | Baker | A61B 3/10 | | |
| | | | 600/318 | | |
| 2008/0228699 A1 * | 9/2008 | Kenedy | G06Q 40/08 | | |
| 2008/0234785 A1 * | 9/2008 | Nakayama | A61B 5/4035 | | |
| | | | 607/62 | | |
| 2009/0288800 A1 * | 11/2009 | Kang | B60N 2/793 | | |
| | | | 165/59 | | |
| 2010/0011502 A1 * | 1/2010 | Brykalski | A47C 21/04 | | |
| | | | 5/423 | | |
| 2010/0100004 A1 * | 4/2010 | van Someren | A61B 5/4818 | | |
| | | | 600/595 | | |
| 2010/0199687 A1 * | 8/2010 | Woods | H10N 10/13 | | |
| | | | 165/181 | | |
| 2010/0324611 A1 * | 12/2010 | Deming | A61N 1/0484 | | |
| | | | 607/2 | | |
| 2011/0015495 A1 * | 1/2011 | Dothie | A47C 31/123 | | |
| | | | 600/300 | | |
| 2011/0073292 A1 * | 3/2011 | Datta | F28F 1/40 | | |
| | | | 165/157 | | |
| 2011/0107514 A1 * | 5/2011 | Brykalski | A47C 21/044 | | |
| | | | 5/652.1 | | |
| 2011/0230790 A1 * | 9/2011 | Kozlov | G04G 13/026 | | |
| | | | 600/595 | | |
| 2011/0267196 A1 * | 11/2011 | Hu | A61B 5/4815 | | |
| | | | 340/575 | | |
| 2012/0072233 A1 * | 3/2012 | Hanlon | G16H 20/60 | | |
| | | | 705/2 | | |
| 2012/0089909 A1 * | 4/2012 | Block | G06Q 10/06 | | |
| | | | 715/764 | | |
| 2012/0159968 A1 * | 6/2012 | Doucet | F25D 31/007 | | |
| | | | 62/157 | | |
| 2012/0221350 A1 * | 8/2012 | Kenedy | G16B 20/00 | | |
| | | | 705/2 | | |
| 2012/0290327 A1 * | 11/2012 | Hanlon | G06Q 30/0271 | | |
| | | | 705/3 | | |
| 2012/0313776 A1 * | 12/2012 | Utter, II | G16H 20/30 | | |
| | | | 340/539.12 | | |
| 2013/0019611 A1 * | 1/2013 | Sims | A41D 13/005 | | |
| | | | 165/41 | | |
| 2013/0030260 A1 * | 1/2013 | Hale | G16H 50/30 | | |
| | | | 600/301 | | |
| 2013/0035949 A1 * | 2/2013 | Saltzman | G06Q 10/06 | | |
| | | | 434/262 | | |

(56) References Cited

U.S. PATENT DOCUMENTS

| | | | |
|---|---|---|---|
| 2013/0060306 A1* | 3/2013 | Colbauch | A61N 5/0618 607/88 |
| 2013/0063550 A1* | 3/2013 | Ritchey | A61B 5/7246 345/207 |
| 2013/0138239 A1* | 5/2013 | Chen | G05B 19/41875 700/121 |
| 2013/0216982 A1* | 8/2013 | Bennett | A61B 5/4866 434/127 |
| 2013/0234823 A1* | 9/2013 | Kahn | G06Q 10/1093 340/3.1 |
| 2014/0067730 A1* | 3/2014 | Kozloski | G16H 20/70 706/12 |
| 2014/0074510 A1* | 3/2014 | McClung | G16H 50/30 705/3 |
| 2014/0076318 A1* | 3/2014 | Flower | A61M 16/0051 128/204.23 |
| 2014/0114680 A1* | 4/2014 | Mills | G16H 50/30 705/2 |
| 2014/0156308 A1* | 6/2014 | Ohnemus | G16H 15/00 705/3 |
| 2014/0208508 A1* | 7/2014 | Mikesell | A47G 9/0223 5/497 |
| 2015/0025809 A1* | 1/2015 | Herron | A23L 33/30 702/19 |
| 2015/0164409 A1* | 6/2015 | Benson | A61B 5/1116 600/595 |
| 2015/0194071 A1* | 7/2015 | Bennett | G16H 20/30 434/127 |
| 2015/0203068 A1* | 7/2015 | Foo | B60R 21/36 701/1 |
| 2015/0220157 A1* | 8/2015 | Marggraff | G06F 3/0485 345/156 |
| 2015/0220697 A1* | 8/2015 | Hunt | G16H 20/60 705/2 |
| 2015/0235562 A1* | 8/2015 | Klein | G09B 5/02 434/127 |
| 2015/0257697 A1* | 9/2015 | Sepah | A61B 5/4815 600/300 |
| 2015/0335420 A1* | 11/2015 | Blum | H04N 23/66 623/6.22 |
| 2015/0366703 A1* | 12/2015 | Du | A61F 7/02 607/104 |
| 2016/0029808 A1* | 2/2016 | Youngblood | F25D 29/00 62/3.2 |
| 2016/0078278 A1* | 3/2016 | Moore | G02B 27/017 345/8 |
| 2016/0103338 A1* | 4/2016 | Hart | A61B 5/163 351/206 |
| 2016/0151603 A1* | 6/2016 | Shouldice | G16H 20/70 600/26 |
| 2016/0217266 A1* | 7/2016 | Damani | G16H 40/67 |
| 2016/0249842 A1* | 9/2016 | Ohana Lubelchick | A61B 5/4803 704/237 |
| 2016/0270717 A1* | 9/2016 | Luna | A61B 5/743 |
| 2016/0310697 A1* | 10/2016 | Franceschetti | A61B 5/0022 |
| 2017/0017759 A1* | 1/2017 | MacNeice | G16H 40/63 |
| 2017/0053068 A1* | 2/2017 | Pillai | G05B 15/02 |
| 2017/0147775 A1* | 5/2017 | Ohnemus | G16H 50/50 |
| 2017/0172730 A1* | 6/2017 | Blum | G02C 7/06 |
| 2017/0176777 A1* | 6/2017 | Blum | A61F 9/061 |
| 2017/0189641 A1* | 7/2017 | Moturu | G16H 20/70 |
| 2017/0249445 A1* | 8/2017 | Devries | A61B 5/7278 |
| 2017/0277841 A1* | 9/2017 | Shankar | G16Z 99/00 |
| 2017/0291067 A1* | 10/2017 | Jang | G09B 19/0092 |
| 2017/0293722 A1* | 10/2017 | Valverde, Jr. | G16H 70/20 |
| 2017/0307907 A1* | 10/2017 | Hart | A61B 3/112 |
| 2017/0323078 A1* | 11/2017 | Michon | G16H 50/30 |
| 2018/0082317 A1* | 3/2018 | Reier | G16H 70/20 |
| 2018/0110960 A1* | 4/2018 | Youngblood | A47C 21/048 |
| 2018/0192136 A1* | 7/2018 | Grabowski | H04N 21/812 |
| 2018/0226155 A1* | 8/2018 | Mahoney | G16H 15/00 |
| 2018/0233064 A1* | 8/2018 | Dunn | G09B 19/0092 |
| 2018/0233223 A1* | 8/2018 | Solari | G16H 20/60 |
| 2018/0260387 A1* | 9/2018 | Ben-Kiki | G06F 40/30 |
| 2018/0268821 A1* | 9/2018 | Levanon | G10L 25/18 |
| 2018/0277248 A1* | 9/2018 | Nazem | G16H 50/30 |
| 2018/0285528 A1* | 10/2018 | Healey | G16H 50/50 |
| 2018/0344215 A1* | 12/2018 | Ohnemus | A61B 5/1118 |
| 2019/0008577 A1* | 1/2019 | Lazarus | A61B 18/14 |
| 2019/0065692 A1* | 2/2019 | Connelly | G16H 50/30 |
| 2019/0099582 A1* | 4/2019 | Crow | A61B 5/02405 |
| 2019/0371452 A1* | 12/2019 | Mainardi | G16H 50/30 |
| 2020/0118685 A1* | 4/2020 | Lee | G16H 50/30 |
| 2020/0143947 A1* | 5/2020 | Choi | A61B 5/7275 |
| 2020/0163824 A1* | 5/2020 | Kim | A61H 15/0078 |
| 2020/0205728 A1* | 7/2020 | Molina | A61B 5/4815 |
| 2021/0012900 A1* | 1/2021 | Smith | G16H 50/30 |
| 2021/0041725 A1* | 2/2021 | Hart | G02C 11/10 |
| 2021/0287803 A1* | 9/2021 | Radrich | G16H 40/67 |
| 2021/0369161 A1* | 12/2021 | Visconti | G06V 40/197 |
| 2022/0028541 A1* | 1/2022 | Paull | G16H 20/10 |
| 2022/0030382 A1* | 1/2022 | Klasson | G06N 5/01 |
| 2022/0308366 A1* | 9/2022 | Hart | A61B 3/112 |
| 2022/0310220 A1* | 9/2022 | Kaput | G16H 40/63 |
| 2022/0310221 A1* | 9/2022 | Kaput | G16H 10/20 |
| 2022/0310228 A1* | 9/2022 | Kaput | G16H 10/20 |
| 2022/0310229 A1* | 9/2022 | Kaput | G06F 3/04847 |
| 2022/0310235 A1* | 9/2022 | Kaput | G06F 9/453 |
| 2022/0310254 A1* | 9/2022 | Kaput | G16H 50/70 |
| 2022/0310264 A1* | 9/2022 | Kaput | G16H 20/10 |
| 2022/0344057 A1 | 10/2022 | Kyyröet al. | |

* cited by examiner

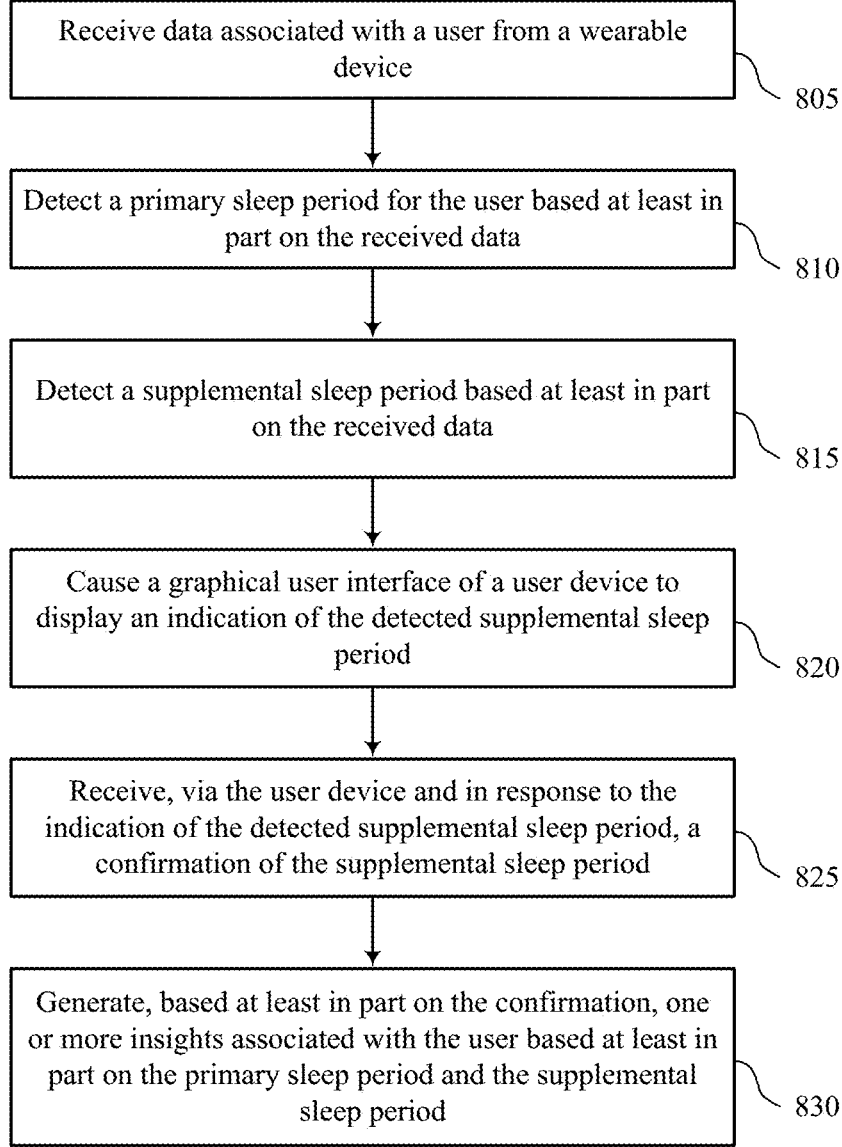

Receive data associated with a user from a wearable device

805

Detect a primary sleep period for the user based at least in part on the received data

810

Detect a supplemental sleep period based at least in part on the received data

815

Cause a graphical user interface of a user device to display an indication of the detected supplemental sleep period

820

Receive, via the user device and in response to the indication of the detected supplemental sleep period, a confirmation of the supplemental sleep period

825

Generate, based at least in part on the confirmation, one or more insights associated with the user based at least in part on the primary sleep period and the supplemental sleep period

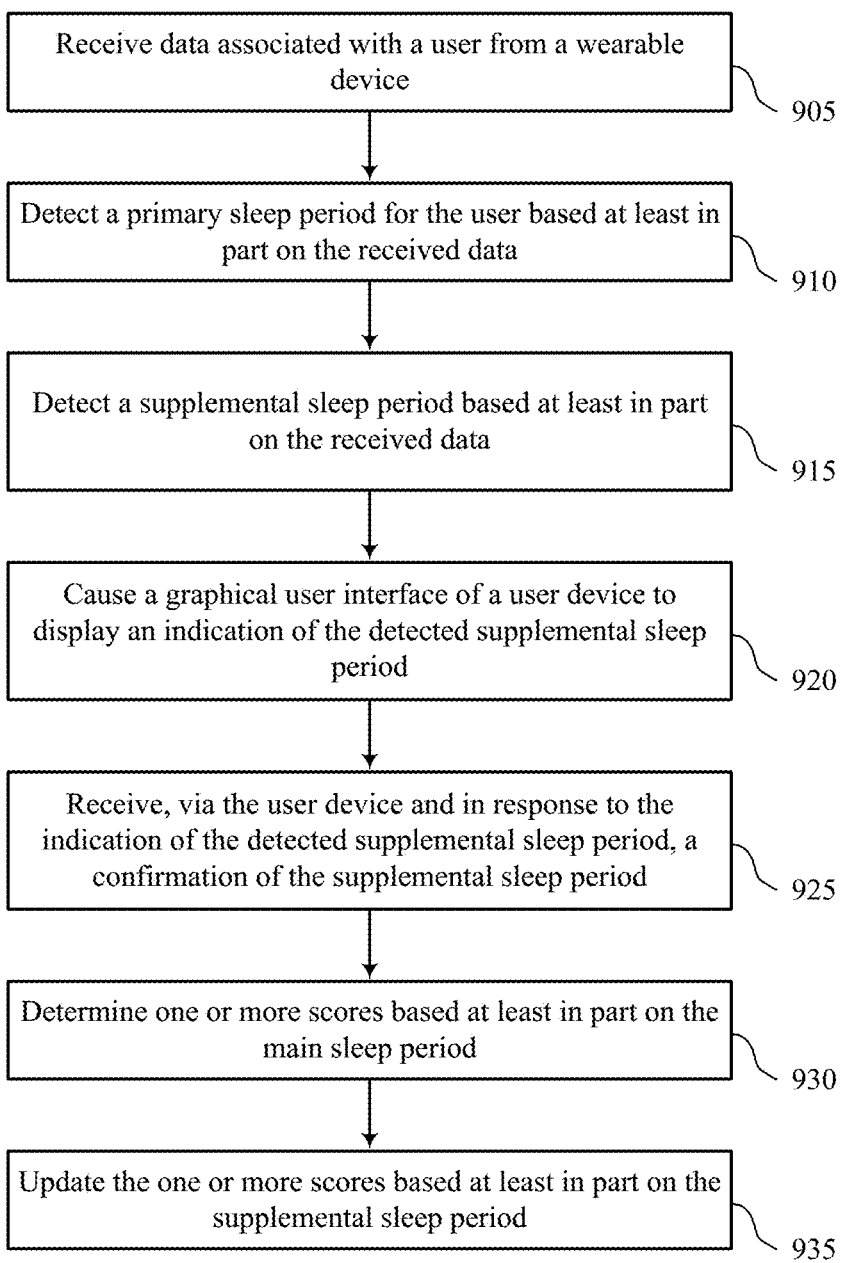

Receive data associated with a user from a wearable device ⟍ 905

Detect a primary sleep period for the user based at least in part on the received data ⟍ 910

Detect a supplemental sleep period based at least in part on the received data ⟍ 915

Cause a graphical user interface of a user device to display an indication of the detected supplemental sleep period ⟍ 920

Receive, via the user device and in response to the indication of the detected supplemental sleep period, a confirmation of the supplemental sleep period ⟍ 925

Determine one or more scores based at least in part on the main sleep period ⟍ 930

Update the one or more scores based at least in part on the supplemental sleep period ⟍ 935

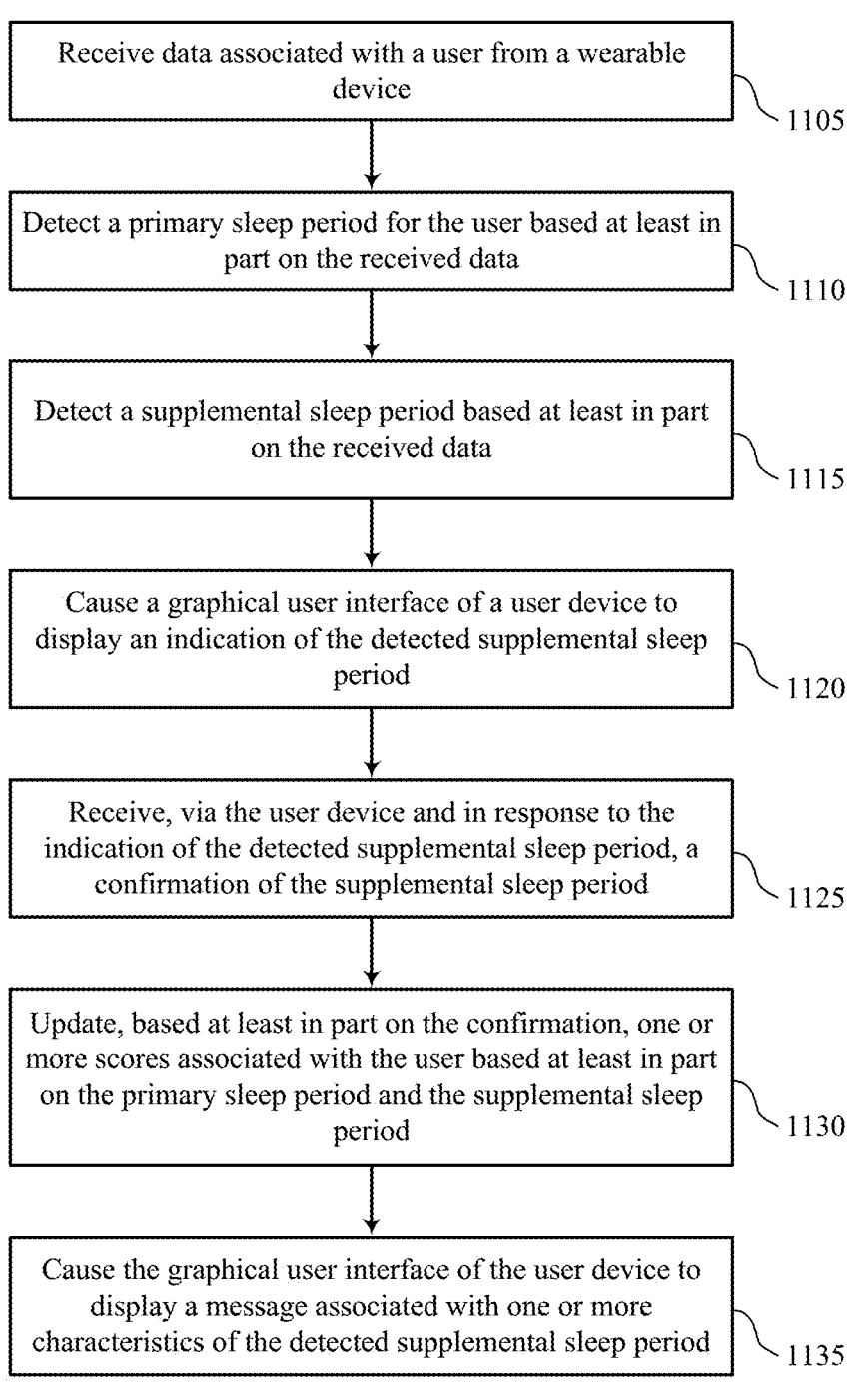

Receive data associated with a user from a wearable device

1105

Detect a primary sleep period for the user based at least in part on the received data

1110

Detect a supplemental sleep period based at least in part on the received data

1115

Cause a graphical user interface of a user device to display an indication of the detected supplemental sleep period

1120

Receive, via the user device and in response to the indication of the detected supplemental sleep period, a confirmation of the supplemental sleep period

1125

Update, based at least in part on the confirmation, one or more scores associated with the user based at least in part on the primary sleep period and the supplemental sleep period

1130

Cause the graphical user interface of the user device to display a message associated with one or more characteristics of the detected supplemental sleep period

METHOD AND SYSTEM FOR SUPPLEMENTAL SLEEP DETECTION

CROSS REFERENCE

The present Application for Patent is a Continuation of U.S. patent application Ser. No. 17/729,557 by KYYRÖ et al., entitled "METHOD AND SYSTEM FOR SUPPLE-MENTAL SLEEP DETECTION," filed Apr. 26, 2022, which claims the benefit of U.S. Provisional Patent Application No. 63/180,381 by KYYRÖ et al., entitled "METHOD AND SYSTEM FOR SUPPLEMENTAL SLEEP DETECTION," filed Apr. 27, 2021, each of which are expressly incorporated by reference herein.

FIELD OF TECHNOLOGY

The following relates generally to wearable devices and data processing, and more specifically to techniques for adjusting Sleep Score and Readiness Score based on multiple sleep periods.

BACKGROUND

Some wearable devices may be configured to collect data from users associated with movement and other activities. For example, some wearable devices may be configured to detect when a user is asleep. However, conventional sleep detection techniques implemented by some wearable devices are deficient.

BRIEF DESCRIPTION OF THE DRAWINGS

FIGS. 8 through 11 show flowcharts illustrating methods that support a method and system for supplemental sleep detection in accordance with aspects of the present disclosure.

DETAILED DESCRIPTION

Figure 1:
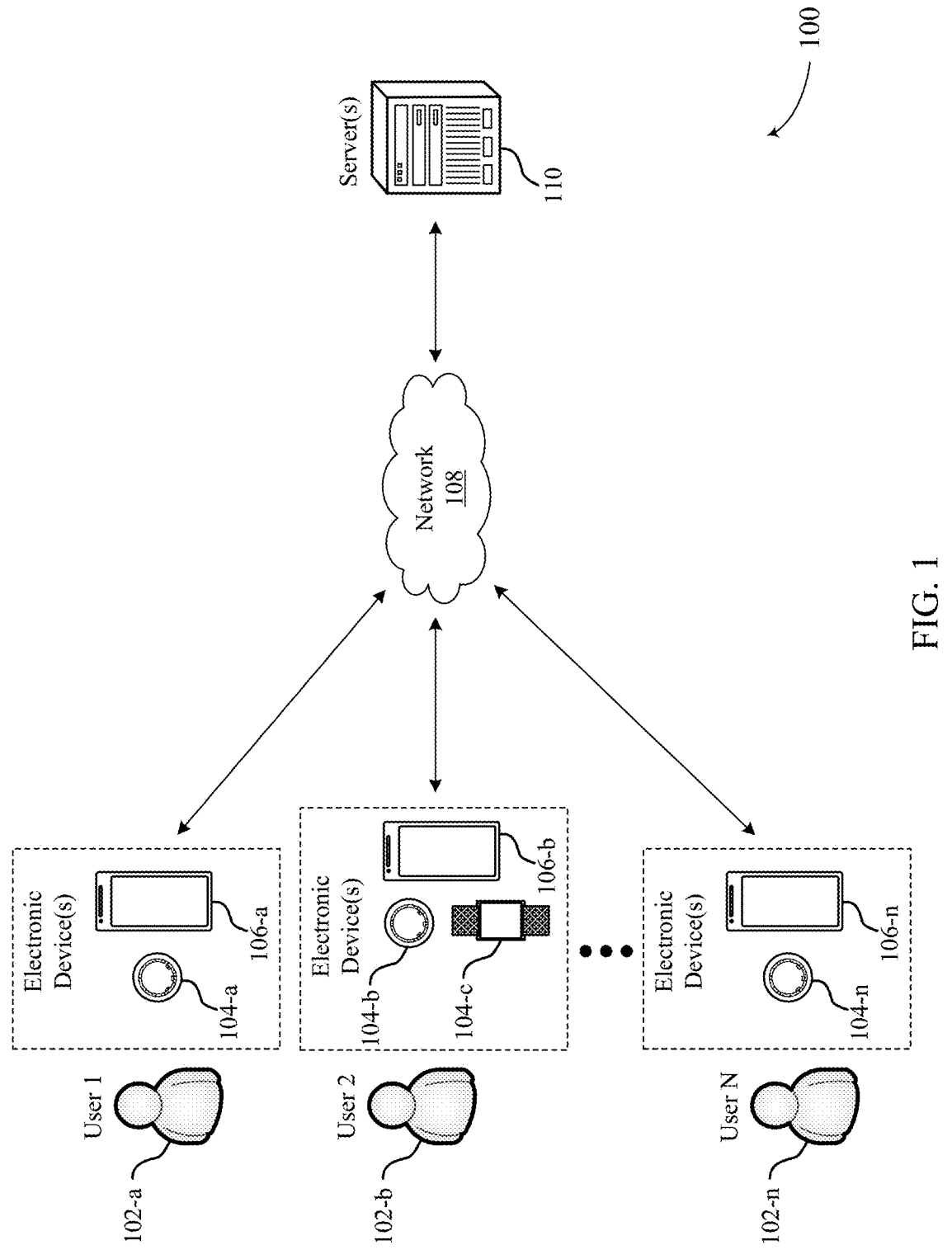
FIG. 1 illustrates an example of a system that supports a method and system for supplemental sleep detection in accordance with aspects of the present disclosure.

Some wearable devices may be configured to collect data from users associated with movement and other activities. For example, some wearable devices may be configured to detect when a user is asleep. However, some conventional wearable devices are only configured to detect when the user is asleep during the night, such as when the user goes to bed at night. In such cases, conventional wearable devices may not accurately track or reflect all the sleep a user receives throughout the day. For example, such wearable devices may not track or recognize naps the user takes during the day. As such, physiological data collected by some wearable devices may not accurately represent the total sleep, rest, and activity the user receives throughout the day, which may result in inaccurate guidance that is provided to the user.

Accordingly, in order to efficiently and accurately track a user's sleep patterns, a wearable device of the present disclosure may be configured to collect sleep data throughout a 24 hour period, including at night and during the daytime. Moreover, wearable devices may be configured to detect multiple sleep durations, including a "primary sleep period" (that is usually at night) as well as supplemental sleep periods, such as naps during the day.

Aspects of the present disclosure are directed to techniques for detecting naps based on data collected by a wearable device. In particular, aspects of the present disclosure are directed to techniques for detecting naps taken by a user, and selectively adjusting scores associated with the user (e.g., Sleep Scores, Readiness Scores) based on the detected naps. For example, a system may receive data (e.g., temperature, heart rate) collected by a wearable device worn by a user, and may determine whether the user has taken (or is currently taking) a nap based on the received data. In some cases, the system may determine the time of the nap relative to a "primary sleep period" for the user. The primary sleep period may be used to generate initial scores for the user, such as a Sleep Score and a Readiness Score, that indicate a relative quality of sleep and a relative measure of readiness, respectively. Upon detecting the nap, the system may selectively adjust the initial scores (e.g., initial Sleep Score, initial Readiness Score) based on characteristics associated with the detected nap (e.g., timing, length, type of sleep).

In some implementations, upon detecting a nap, the system may prompt the user to confirm whether the user took a nap or not, and may selectively adjust Sleep Score and Readiness Score when the user confirms that they took a nap. In some implementations, a detected nap may be used to selectively adjust each individual contributing factor that is used to adjust the respective Sleep Score and Readiness Score. In some aspects, the timing of the detected nap relative to the primary sleep period for the user may be used to determine whether the detected nap may be used to adjust scores (e.g., Sleep Score, Readiness Score) for the user for the day that the nap took place, or the following day. In some implementations, the system may generate messages (e.g., insights, alerts) for the user based on the detected nap, where the alerts indicate how the detected nap affected the user's respective scores. The generated alerts may additionally, or alternatively, provide other insights regarding the nap, such as whether the timing and/or duration of the nap was beneficial for the user, whether the user should consider adjusting a timing and/or duration of naps, and the like.

While much of the present disclosure is described in the context of updating Sleep Scores and Readiness Scores based on detected supplemental sleep periods, this is not to be regarded as a limitation of the present disclosure. Indeed, it is contemplated herein that data associated with a supplemental sleep period of a user may be used to update any score, measure, metric, or other abstraction associated with a user's health or activity.

Aspects of the disclosure are initially described in the context of a system supporting supplemental sleep detection. Additional aspects of the disclosure are described in the context of an example timing diagram and an example graphical user interface (GUI). Aspects of the disclosure are further illustrated by and described with reference to apparatus diagrams, system diagrams, and flowcharts that relate to a method and system for supplemental sleep detection.

FIG. 1 illustrates an example of a system for nap detection based on data collected by a wearable device, in accordance with aspects of the present disclosure. The system 100 includes a plurality of electronic devices (e.g., wearable devices 104, user devices 106) that may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.) and user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, which may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of which may measure physiological parameters and some of which may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-a (User 1) may operate, or may be associated with, a wearable device 104-a (e.g., ring 104-a) and a user device 106-a that may operate as described herein. In this example, the user device 106-a associated with user 102-a may process/store physiological parameters measured by the ring 104-a. Comparatively, a second user 102-b (User 2) may be associated with a ring 104-b, a watch wearable device 104-c (e.g., watch 104-c), and a user device 106-b, where the user device 106-b associated with user 102-b may process/store physiological parameters measured by the ring 104-b and/or the watch 104-c. Moreover, an nth user 102-n (User N) may be associated with an arrangement of electronic devices described herein (e.g., ring 104-n, user device 106-n). In some aspects, wearable devices 104 (e.g., rings 104, watches 104) and other electronic devices may be communicatively coupled to the user devices 106 of the respective users 102 via Bluetooth, Wi-Fi, and other wireless protocols.

In some implementations, the rings 104 (e.g., wearable devices 104) of the system 100 may be configured to collect physiological data from the respective users 102 based on arterial blood flow within the user's finger. In particular, a ring 104 may utilize one or more LEDs (e.g., red LEDs, green LEDs) which emit light on the palm-side of a user's finger to collect physiological data based on arterial blood flow within the user's finger. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices which utilize LEDs which are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-*a* associated with the first user 102-*a* may be communicatively coupled to the user device 106-*a*, where the user device 106-*a* is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time during which a user 102 is asleep, and classify periods of time during which the user 102 is asleep into one or more sleep stages (e.g., sleep stage classification). For example, as shown in FIG. 1, User 102-*a* may be associated with a wearable device 104-*a* (e.g., ring 104-*a*) and a user device 106-*a*. In this example, the ring 104-*a* may collect physiological data associated with the user 102-*a*, including temperature, heart rate, HRV, respiratory rate, and the like. In some aspects, data collected by the ring 104-*a* may be input to a machine learning classifier, where the machine learning classifier is configured to determine periods of time during which the user 102-*a* is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-*a* via a GUI of the user device 106-*a*. Sleep stage classification may be used to provide feedback to a user 102-*a* regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle, which repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-*a* via the wearable device 104-*a*. In this example, the circadian rhythm adjustment model may be configured to "weight," or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models which are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state; 2) circadian rhythms; 3) non-endogenous daily rhythms shown to be imposed on top of circadian rhythms, as in work schedules; 4) weekly rhythms, or other artificial time periodicities exogenously imposed (e.g., in a hypothetical culture with 12 day "weeks", 12 day rhythms could be used); 5) multi-day ovarian rhythms in women and spermatogenesis rhythms in men; 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

In some aspects, the respective devices of the system 100 may support techniques for detecting naps based on data collected by a wearable device. In particular, the system 100 illustrated in FIG. 1 may support techniques for detecting naps taken by a user, and selectively adjusting scores associated with the user (e.g., Sleep Scores, Readiness Scores) based on the detected naps. For example, as shown in FIG. 1, User 1 may be associated with a wearable device (e.g., ring) and a mobile device. In this example, the ring may collect data associated with the user, including temperature, heart rate, HRV, and the like. In some aspects, data collected by the ring may be used to determine whether User 1 has taken (or is currently taking) a nap. Detection of a nap may be performed by any of the components of the system 100, including the ring, the mobile device associated with User 1, the one or more servers, or any combination thereof. In some cases, detection of a nap may be based on user input (e.g., a user may manually input or tag a nap). For example, User 1 may take a nap (e.g., while not wearing the ring) and may input data associated with the nap such as when the nap was taken, a duration of the nap, feedback associated with the nap (e.g., perceived quality of the nap, how rested User 1 felt after the nap, etc.), or the like thereof. Additionally, or alternatively, detection of a nap may be based on one or more other wearable devices. For example, User 1 may wear a watch wearable device and the system 100 may detect a nap based on data received from the watch wearable device. In this regard, as will be described herein, aspects of the present disclosure may enable the system 100 to detect naps based on physiological data collected via the ring 104, based on user-inputs (e.g., a user manually inputting a nap), based on physiological data collected via other wearable devices, or any combination thereof, where detected naps may be used to update information (e.g., Sleep Score, Readiness Score) associated with the user.

In some cases, the timing of a detected nap may be determined relative to a "primary sleep period" for User 1, where the primary sleep period is used to generate initial scores (e.g., initial Sleep Score, initial Readiness Score) for User 1. Upon detecting the nap, the system 100 may selectively adjust the initial scores (e.g., initial Sleep Score, initial Readiness Score) based on characteristics associated with the detected nap (e.g., timing, length, type of sleep).

In some implementations, upon detecting a nap, the system 100 may prompt User 1 (e.g., via a GUI of the mobile device) to confirm whether the user took a nap or not, and may selectively adjust Sleep Score and Readiness Score only when the user confirms that they took a nap. In some implementations, a detected nap may be used to selectively adjust each individual contributing factor that is used to adjust the respective Sleep Score and Readiness Score. In some aspects, the timing of the detected nap relative to the primary sleep period for User 1 may be used to determine whether the detected nap may be used to adjust scores (e.g., Sleep Score, Readiness Score) for User 1 for the day that the nap took place, or the following day. In some implementations, the system 100 may generate alerts for User 1 (e.g., via the ring, mobile device, or both) based on the detected nap, where the alerts indicate how the detected nap affected the respective scores. The generated alerts may additionally, or alternatively, provide other insights regarding the nap, such as whether the timing and/or duration of the nap was beneficial for User 1, whether User 1 should consider adjusting a timing and/or duration of naps, and the like.

Techniques described herein may provide for improved sleep tracking using data collected by a wearable device. In particular, techniques described herein may be used to detect multiple sleep periods for a given user, including primary sleep periods and supplemental sleep periods (i.e. naps), which may be used to generate more accurate and comprehensive scores (e.g., Sleep Scores, Readiness Scores) for the user. By providing a user with a more comprehensive evaluation of their sleep patterns, techniques described herein may enable the user to effectively adjust their sleep patterns, which may improve the sleep quality and overall health for the user.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
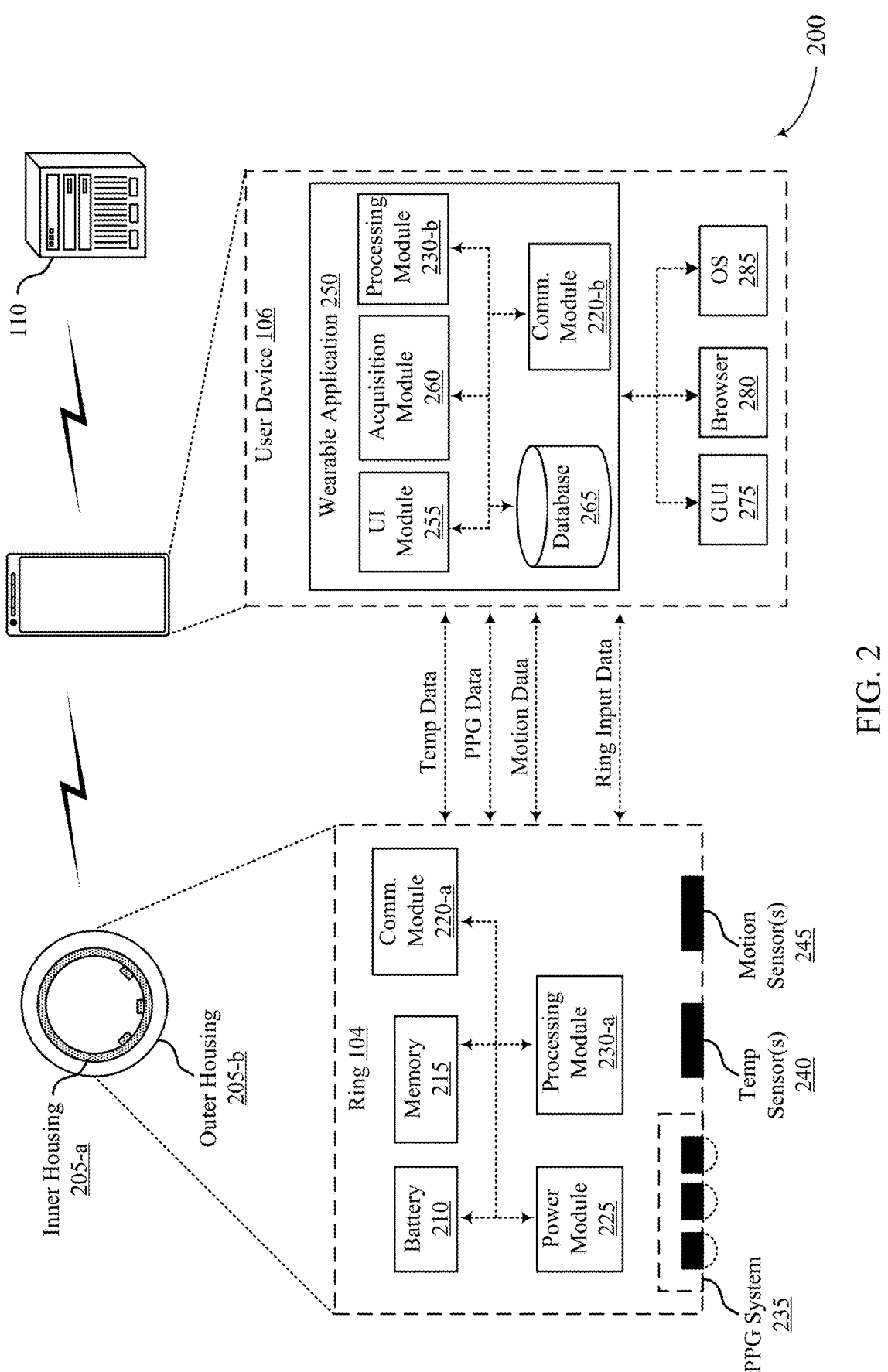
FIG. 2 illustrates an example of a system that supports a method and system for supplemental sleep detection in accordance with aspects of the present disclosure.

FIG. 2 illustrates an example of a system 200 that supports a method and system for supplemental sleep detection in accordance with aspects of the present disclosure. The system 200 may implement, or be implemented by, system 100. In particular, system 200 illustrates an example of a ring as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels, and the like.

The system 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, PPG data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205, which may include an inner housing 205-*a* and an outer housing 205-*b*. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-a, a memory 215, a communication module 220-a, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components which are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using a clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-b component (e.g., a shell) and an inner housing 205-a component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-b (e.g., a metal outer housing 205-b). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate (s) from water and/or other chemicals.

The outer housing 205-b may be fabricated from one or more materials. In some implementations, the outer housing 205-b may include a metal, such as titanium, which may provide strength and abrasion resistance at a relatively light weight. The outer housing 205-b may also be fabricated from other materials, such polymers. In some implementations, the outer housing 205-b may be protective as well as decorative.

The inner housing 205-a may be configured to interface with the user's finger. The inner housing 205-a may be formed from a polymer (e.g., a medical grade polymer) or other material. In some implementations, the inner housing 205-a may be transparent. For example, the inner housing 205-a may be transparent to light emitted by the PPG light emitting diodes (LEDs). In some implementations, the inner housing 205-a component may be molded onto the outer housing 205-a. For example, the inner housing 205-a may include a polymer that is molded (e.g., injection molded) to fit into an outer housing 205-b metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-*a* of the ring 104 may include one or more processors (e.g., processing units), microcontrollers, digital signal processors, systems on a chip (SOCs), and/or other processing devices. The processing module 230-*a* communicates with the modules included in the ring 104. For example, the processing module 230-*a* may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-*a* may communicate with the memory 215. The memory 215 may include computer-readable instructions that, when executed by the processing module 230-*a*, cause the processing module 230-*a* to perform the various functions attributed to the processing module 230-*a* herein. In some implementations, the processing module 230-*a* (e.g., a microcontroller) may include additional features associated with other modules, such as communication functionality provided by the communication module 220-*a* (e.g., an integrated Bluetooth Low Energy transceiver) and/or additional onboard memory 215.

The communication module 220-*a* may include circuits that provide wireless and/or wired communication with the user device 106 (e.g., communication module 220-*b* of the user device 106). In some implementations, the communication modules 220-*a*, 220-*b* may include wireless communication circuits, such as Bluetooth circuits and/or Wi-Fi circuits. In some implementations, the communication modules 220-*a*, 220-*b* can include wired communication circuits, such as Universal Serial Bus (USB) communication circuits. Using the communication module 220-*a*, the ring 104 and the user device 106 may be configured to communicate with each other. The processing module 230-*a* of the ring may be configured to transmit/receive data to/from the user device 106 via the communication module 220-*a*. Example data may include, but is not limited to, motion data, temperature data, pulse waveforms, heart rate data, HRV data, PPG data, and status updates (e.g., charging status, battery charge level, and/or ring 104 configuration settings). The processing module 230-*a* of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors which may be used to collect data in addition to, or which supplements, data collected by the ring 104 itself. Moreover, a charger or other power source for the ring 104 may function as a user device 106, in which case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during 104 charging. The power module 225 may also regulate voltage(s) of the device electronics, regulate power output to the device electronics, and monitor the state of charge of the battery 210. In some implementations, the battery 210 may include a protection circuit module (PCM) that protects the battery 210 from high current discharge, over voltage during 104 charging, and under voltage during 104 discharge. The power module 225 may also include electro-static discharge (ESD) protection.

The one or more temperature sensors 240 may be electrically coupled to the processing module 230-*a*. The temperature sensor 240 may be configured to generate a temperature signal (e.g., temperature data) that indicates a temperature read or sensed by the temperature sensor 240. The processing module 230-*a* may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-*a*) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-*a* may use to determine the temperature. As another example, in cases where the temperature sensor 240 includes a passive sensor, the processing module 230-*a* (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-*a* may sample the user's temperature over time. For example, the processing module 230-*a* may sample the user's temperature according to a sampling rate. An example sampling rate may include one sample per second, although the processing module 230-*a* may be configured to sample the temperature signal at other sampling rates that are higher or lower than one sample per second. In some implementations, the processing module 230-*a* may sample the user's temperature continuously throughout the day and night. Sampling at a sufficient rate (e.g., one sample per second) throughout the day may provide sufficient temperature data for analysis described herein.

The processing module 230-*a* may store the sampled temperature data in memory 215. In some implementations, the processing module 230-*a* may process the sampled temperature data. For example, the processing module 230-*a* may determine average temperature values over a period of time. In one example, the processing module 230-*a* may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, which may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during 104 exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-a near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-a may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-a may sample the sensors at different rates and average/store different values for the different sensors. In some implementations, the processing module 230-a may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-a may sample the PPG signal and determine a user's pulse waveform based on the PPG signal. The processing module 230-a may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 in which the optical receiver(s) receive transmitted light that is reflected through the region of the user's finger. In some implementations, the PPG system 235 may be configured as a transmissive PPG system 235 in which the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-a may control one or both of the optical transmitters to transmit light while sampling the PPG signal generated by the optical receiver. In some implementations, the processing module 230-a may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform, which may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-*a* may store the pulse waveform in memory 215 in some implementations. The processing module 230-*a* may process the pulse waveform as it is generated and/or from memory 215 to determine user physiological parameters described herein.

The processing module 230-*a* may determine the user's heart rate based on the pulse waveform. For example, the processing module 230-*a* may determine heart rate (e.g., in beats per minute) based on the time between peaks in the pulse waveform. The time between peaks may be referred to as an interbeat interval (IBI). The processing module 230-*a* may store the determined heart rate values and IBI values in memory 215.

The processing module 230-*a* may determine HRV over time. For example, the processing module 230-*a* may determine HRV based on the variation in the IBIs. The processing module 230-*a* may store the HRV values over time in the memory 215. Moreover, the processing module 230-*a* may determine the user's respiratory rate over time. For example, the processing module 230-*a* may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-*a* may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BM1160 inertial micro electro-mechanical system (MEMS) sensor that may measure angular rates and accelerations in three perpendicular axes.

The processing module 230-*a* may sample the motion signals at a sampling rate (e.g., 50 Hz) and determine the motion of the ring 104 based on the sampled motion signals. For example, the processing module 230-*a* may sample acceleration signals to determine acceleration of the ring 104. As another example, the processing module 230-*a* may sample a gyro signal to determine angular motion. In some implementations, the processing module 230-*a* may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-*a* may compress the data stored in memory 215. For example, the processing module 230-*a* may delete sampled data after making calculations based on the sampled data. As another example, the processing module 230-*a* may average data over longer periods of time in order to reduce the number of stored values. In a specific example, if average temperatures for a user over one minute are stored in memory 215, the processing module 230-*a may calculate average temperatures over a five minute time period for storage, and then subsequently erase the one minute average temperature data. The processing module 230**-*a* may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during 104 portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/ systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS), a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") which may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-*b*, a communication module 220-*b*, and a storage module (e.g., database 265) configured to store application data.

The various data processing operations described herein may be performed by the ring 104, the user device 106, the servers 110, or any combination thereof. For example, in some cases, data collected by the ring 104 may be pre-processed and transmitted to the user device 106. In this example, the user device 106 may perform some data processing operations on the received data, may transmit the data to the servers 110 for data processing, or both. For instance, in some cases, the user device 106 may perform processing operations which require relatively low process-ing power and/or operations which require a relatively low latency, whereas the user device 106 may transmit the data to the servers 110 for processing operations which require relatively high processing power and/or operations which may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., Sleep Score, Readiness Score) for the user based on the collected data. For example, as noted previously herein, the ring 104 of the system 200 may be worn by a user to collect data from the user, including temperature, heart rate, HRV, and the like. Data collected by the ring 104 may be used to deter-mine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent cal-endar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner which is consistent with their sleep schedules. In some cases, users may be able to selectively adjust (e.g., via the GUI) a timing of sleep days relative to calendar days so that the sleep days are aligned with the duration of time in which the respective users typically sleep.

In some implementations, each overall score for a user for each respective day (e.g., Sleep Score, Readiness Score) may be determined/calculated based on one or more "con-tributors," "factors," or "contributing factors." For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contribu-tor may refer to a sum total of deep sleep durations across all sleep periods of the sleep day including deep sleep. The "latency" contributor may signify how long (e.g., average, median, longest) the user takes to go to sleep, and may be calculated using the average of long sleep periods through-out the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some aspects, the ring, mobile device, and servers of the system 200 may be configured to evaluate sleep patterns for a user. In particular, the respective components of the system 200 may be used to determine what effect naps have on respective scores (e.g., Sleep Scores, Readiness Scores) for a user.

For example, as noted previously herein, the ring of the system 200 may be worn by a user to collect data from the user, including temperature, heart rate, HRV, and the like. Data collected by the ring may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring during the respective sleep day. Scores may include, but are not limited to, Sleep Scores, Readiness Scores, and the like. Sleep days may be further shown and described with reference to FIG. 3.

Figure 3:
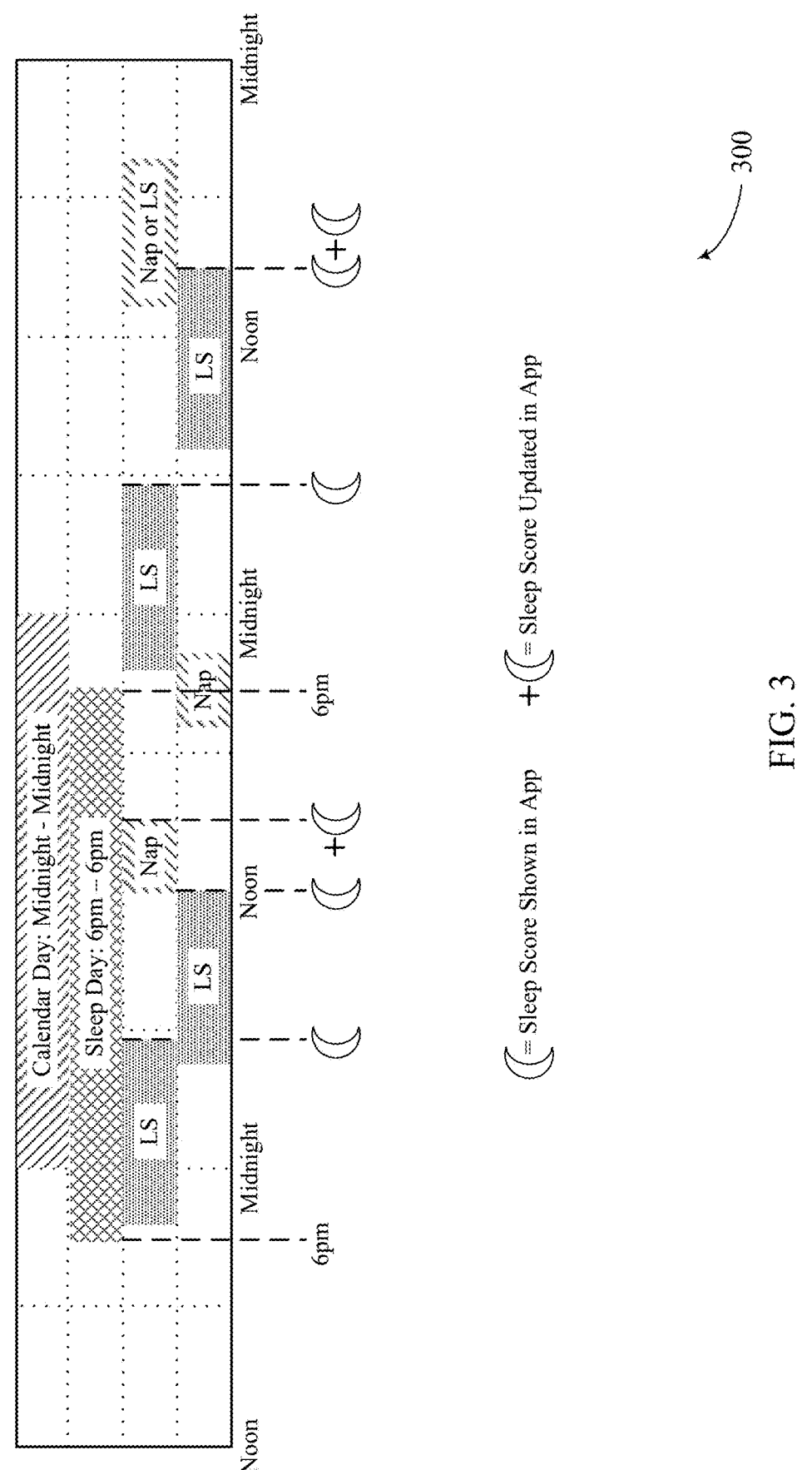
FIG. 3 illustrates an example of a timing diagram that supports a method and system for supplemental sleep detection in accordance with aspects of the present disclosure.

FIG. 3 illustrates an example of a timing diagram 300 that supports a method and system for supplemental sleep detection in accordance with aspects of the present disclosure. The timing diagram 300 may implement, or be implemented by, aspects of the system 100, system 200, or both.

The timing diagram 300 shown in FIG. 3 illustrates a relative timing of "sleep days" relative to traditional calendar days. In particular, the timing diagram 300 illustrates sleep cycles (e.g., cycles of primary sleep periods and supplemental sleep periods) for a first user (row second from the bottom) and a second user (bottom row) throughout two sleep days.

In some cases, "sleep days" may align with the traditional calendar days, such that a given sleep day runs from midnight to midnight of the respective calendar day. In other cases, sleep days may be offset relative to calendar days. For example, as shown in timing diagram 300, sleep days may run from 6:00 pm (18:00) of a calendar day until 6:00 pm (18:00) of the subsequent calendar day. In this example, 6:00 pm may serve as a "cut-off time," where naps and other sleep periods before 6:00 pm are counted for the current sleep day, and sleep periods after 6:00 pm are counted for the subsequent sleep day. Due to the fact that most individuals sleep the most at night, offsetting sleep days relative to calendar days may enable the system 200 to evaluate sleep patterns for users in such a manner that is consistent with their sleep schedules. In some cases, users may be able to selectively adjust (e.g., via the GUI) a timing of sleep days relative to calendar days so that the sleep days are aligned with the duration of time in which the respective users typically sleep.

In some cases, system 200 (e.g., ring, mobile device, server) may determine a longest sleep (LS) period for the user over a twenty-four hour "sleep day" in order to determine initial scores associated with the user's sleep throughout the sleep day, including an initial Sleep Score, an initial Readiness Score, or both. For example, in cases where sleep days run from 6:00 pm to 6:00 pm, the ring may collect data that is used by the mobile device and/or server to detect that the user slept from 10:00 pm (21:00) until 6:00 am (8 hours), and may identify this sleep period as the "primary sleep period" (e.g., longest sleep period) for the user for the respective sleep day. In this example, the system 200 may determine a Sleep Score and Readiness Score for the user for the respective sleep day based on data collected throughout the primary sleep period.

In some implementations, the longest sleep period, or "primary sleep period" must be greater than or equal to three hours to be classified as a "primary sleep period." If there are no sleep periods longer than three hours within a given sleep day, the sleep period with the longest duration may be classified or used as the longest sleep period, or primary sleep period, within the sleep day. In some aspects, the mobile device and/or servers of the system 200 may be configured to dynamically update labels or classifications used to classify sleep periods (e.g., primary sleep period, normal sleep period, supplemental sleep period (nap)). For example, a sleep period that is classified as the primary sleep period (e.g., longest sleep period) may subsequently be classified as a normal (e.g., non-longest) sleep period when the user subsequently sleeps for a longer duration of time within the same sleep day.

In some cases, a user's Sleep Score may not be displayed (e.g., may not be visible or accessible) during at least a portion of a given sleep day. For example, as shown in timing diagram 300, a user's Sleep Score may not be visible between 6:00 pm (18:00) and midnight. In some implementations, the user's Sleep Score may not be displayed during at least a portion of a given sleep day in order to prevent the system from "rewarding" the user for sleep habits that may be detrimental in the long term. For example, as noted herein, studies have found that frequent naps after 6:00 pm may be associated with negative health effects. As such, by refraining from displaying a user's Sleep Score between 6:00 pm and midnight, users who take naps after 6:00 pm will not be immediately "rewarded" for naps after 6:00 pm, which may help reinforce healthy sleeping habits.

In some implementations, each overall score for a user for each respective day (e.g., Sleep Score, Readiness Score) may be determined/calculated based on one or more "contributors," "factors," or "contributing factors." For example, a user's overall Sleep Score may be calculated based on a set of contributors, including: total sleep, efficiency, restfulness, rapid eye movement (REM) sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods, and summed with one extra wake-up for each period), excessive movement, and a "got up count" (e.g., sum of all the got-ups (when user gets out of bed) detected during the different sleep periods, and summed with one extra "get up" for each period).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period. Lastly, the "timing" contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period. For example, a user may nap between 6:00 pm and 7:00 pm, go to a party, sleep between 2:00 am and 9:00 am, and then nap again between 1:00 pm and 2:00 pm, all within the same 24-hour "sleep day." In this example, the sleep periods between 2:00-9:00 am and 1:00-2:00 pm may be used to calculate the heart rate contributor, whereas the sleep period between 6:00-7:00 pm may be discarded for purposes of calculating the heart rate contributor.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). For instance, a user may nap between 6-7 pm, go to a party, then sleep between 2-9 am. The user may then nap between 1-2 pm, all within the same sleep day. In this example, the nap from the previous night between 6-7 pm would not be used for the calculation of the HRV balance contributor. The "recovery index" contributor may be calculated based on the longest sleep period. Recovery index measures how long it takes for a user's resting heart rate to stabilize during the night. A sign of a very good recovery is that a user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some cases, the system 200 may use only the primary sleep period within a respective sleep day to calculate Sleep Score and Readiness Score. However, doing so may result in an incomplete picture of a user's sleep throughout the sleep day, as these scores may not account for other sleep periods (e.g., naps) that take place outside of the primary sleep period. This may especially be the case for users with irregular sleep patterns due to irregular work schedules, nighttime work shifts, medical conditions, or tendencies for polyphasic sleep. In such cases, calculating Readiness Scores and Sleep Scores based only on the primary sleep period for a given day may provide the user with inaccurate, or incomplete, information, as these scores would be calculated based on only a fraction of the total sleep time during the sleep day. According to some studies, roughly a third of Americans take a nap on an average day, such that supplemental sleep periods factor into a significant portion of the population's daily sleep.

Accordingly, the system 200 may be configured to detect multiple sleep periods within a sleep day, including primary sleep periods and supplemental sleep periods (e.g., naps). Moreover, the system 200 may be configured to adjust Sleep Scores and Readiness Scores based on naps detected throughout the sleep day. In addition to supporting a diverse group of users, being able to detect sleep periods outside of the primary sleep period may provide more accurate sleep information to the users, and may improve business-to-business (B2B) use cases, such as sleep coaching and illness detection initiatives.

For the purposes of the present disclosure, the terms "naps," "nap periods," "supplemental sleep periods," and like terms, may be used interchangeably. In some cases, the system 200 (e.g., mobile device, server) may be configured to receive data from the ring, which is collected by a user, and identify periods during which the user is determined to be asleep outside of the primary sleep period as a nap, or a supplemental sleep period. In some cases, any supplemental sleep period that is greater than or equal to a first time duration threshold (e.g., 15 minutes) and less than a second time duration threshold (e.g., 3 hours) may be classified as a supplemental sleep period (e.g., nap). However, it is contemplated herein that other time duration thresholds may be used to classify naps.

In some aspects, a timing of supplemental sleep periods may be determined relative to the primary sleep period for each respective sleep day. In other words, the primary sleep period for a given sleep day may serve as an "anchor" to which supplemental sleep periods may be compared. Naps may be evaluated in relation to the primary sleep period, and may contribute less to the user's overall scores as compared to the primary sleep period. In particular, the mobile device and/or servers of system 200 may be configured to determine whether a detected supplemental sleep period is detected before or after the primary sleep period for the respective sleep day. Whether a nap (e.g., supplemental sleep period) occurs before the primary sleep period (e.g., "early nap") or after the primary sleep period (e.g., "late nap") may determine whether the system 200 will use the data for the nap to update scores determined based on the primary sleep period, or if the system 200 will store the data for the nap for future processing. In some cases, the term "late nap" may refer to a nap that occurs at the beginning of a new sleep day (e.g., after 6:00 pm in the timing diagram 300).

For example, referring to timing diagram 300, sleep days may be defined by the 24 hour period running from 6:00 pm to 6:00 pm, and a first user may sleep from 10:00 pm to 6:00 am within a first sleep day. As such, the primary sleep period for the first user during the first sleep day may be defined from 10:00 pm to 6:00 am. In this example, the mobile device and/or servers may calculate scores (e.g., initial Sleep Score, initial Readiness Score) for the first user for the first sleep day based on the primary sleep period. Subsequently, the first user may take a nap (e.g., supplemental sleep period) between noon and 1:30 pm. In this example, due to the fact that the nap occurred after the primary sleep period (and after initial scores had been calculated), the mobile device and/or servers may be configured to update (e.g., instantly update) the initial scores for the user for that sleep day using the data collected by the ring during the nap.

Conversely, by way of another example and continuing with reference to FIG. 3, a second user may take a nap from 9:00 pm to 10:30 pm on a second sleep day. In this example, the user may be informed that the nap will be taken into account following the next long sleep period (e.g., primary sleep period) for the respective sleep day. Subsequently the second user may sleep from 5:00 am to noon within the second sleep day. As such, the primary sleep period for the second user during the second sleep day may be defined from 5:00 am to noon. In this example, because the nap occurred prior to the primary sleep period for the second user on the second sleep day, and therefore prior to calculation of initial Sleep/Readiness Scores, the mobile device and/or servers record (e.g., store, save) the data from the nap until after the primary sleep period is detected. For instance, the mobile device/servers may calculate scores (e.g., initial Sleep Score, initial Readiness Score) for the second user for the second sleep day based on the primary sleep period, and may subsequently update the initial scores for the user for that sleep day using the data from the nap that occurred prior to the primary sleep period. In other words, in some implementations, the system 200 may not be configured to calculate Sleep Scores and/or Readiness Scores for a user within a given sleep day until the primary sleep period for the user within the respective sleep day is detected. In such cases, data from "early naps" may be tallied up with data from the subsequent primary sleep period. The user may be able to view data associated with the nap (e.g., hypnogram, sleep stages, heart rate, HRV) prior to the primary sleep period, but the data from the nap may not be used to update scores until after the primary sleep period.

In some aspects, refraining from calculating full Sleep Scores and Readiness Scores using naps (e.g., late naps) that occur prior to a primary sleep period may prevent generating/displaying inaccurate scores. Additionally, waiting to tally up effects of late naps until the morning and/or after a late sleep period may prevent reinforcing negative sleep patterns, and may reduce a frequency of late naps (which have been shown to have a detrimental effect to overall sleep).

The timing of naps within a sleep day relative to the primary sleep period for the sleep day may also affect a time at which the nap is recorded, or otherwise viewable by the user in the ring application. For example, User 1 may sleep five hours between 2:00 and 7:00 am. In this example, User 1 goes to his morning shift and works until 4:00 pm (16:00). When User 1 gets home, he sleeps for 2 hours. When User 1 wakes up and opens the ring application on his mobile device, the two hour long nap may have been used to instantly update his Sleep Score and Readiness Score upon confirming the nap. Because sleep during the night was short, the improvement in scores may be moderate, and the effects of the nap may be displayed to the user via messages (e.g., insights) displayed via the GUI.

By way of another example, User 2 works night shifts every second week. On a Sunday afternoon User 2 sleeps for 3 hours between 7:00 pm and 10:00 pm, then heads out for their first night shift of the week. Because the sleep period is 3 hours long, it is not classified as a late nap, but instead is classified as the longest sleep period of the current sleep day, which results in a fairly poor Sleep Score and Readiness Score for the user. Upon coming home the next morning (but within the same sleep day), User 2 sleeps for 5 hours between 9:00 am and 3:00 pm. Upon opening the ring application, the additional 5 hours of sleep in the morning will be shown as having been added to User 2's total Sleep Score and Readiness Score for the sleep day. In this example, the sleep period between 9:00 am and 3:00 pm may be determined to be the longest sleep period, and may therefore be classified as the primary sleep period. Moreover, the previous sleep period between 7:00 pm and 10:00 pm may be re-classified as a nap due to the detection of a longer sleep period within that sleep day. In this regard, in this example, User 2 may not be required to confirm a separate nap "prompt," as the subsequent sleep period was classified as the primary sleep period.

Being able to track supplemental sleep periods (e.g., naps) may improve evaluation of sleeping patterns (e.g., improve sleep tracking accuracy) for users who may not have the luxury of a consistent sleep schedule, such as law enforcement, medical staff, defense employees, new parents, biohackers, and the like. Nap detection techniques supported by the system 200 align with many commonly held beliefs regarding sleep: humans are diurnal animals (e.g., active during the day, rest at night); all sleep is sleep (naps should be taken into account); regular sleep patterns are better than irregular sleep patterns; sleep is how users get ready for the following day; sleep is when users recover from the past day. All humans, irrespective of culture or geographical location, have a genetically hardwired dip in alertness that occurs in the midafternoon hours. Studies have shown that, when done correctly and at the correct time, napping has many benefits including lowering blood pressure, improving memory recall and motor memory, improving awareness (e.g., awareness for driving late at night and/or working night shifts), and the like.

However, excessive daytime sleeping (e.g., napping) may also result in detrimental effects. In particular, excessive napping has been found to have a strong correlation with issues related to sleep health, such as insomnia, apnea, and even more serious conditions such as cardiovascular disease. Additionally or alternatively, sleep patterns, such as excessive napping, may be associated with issues related to mental health, such as depression or anxiety. Accordingly, as will be described herein, system 200 may be configured to generate alerts and provide insights that indicate characteristics of detected naps, and inform users of benefits (and/or detriments) to their sleep patterns and overall health as a result of detected naps.

In some aspects, nap detection allows users to get "credit" for sleep outside of their longest sleeping period (e.g., outside of the primary sleep period). Sleep periods that are outside of the primary sleep period and which satisfy some threshold time duration (e.g., 15 minutes or more of cumulative light, deep, and REM sleep) may be referred to (e.g., classified) as naps, and their contribution to Sleep Score and Readiness Score may be calculated in relation to the primary sleep period. Data collected by the ring during a nap may be used to generate most of the same data (via the ring) as the primary sleep period, including the score deltas, hypnograms, sleep stages, heart rate graphs, HRV graphs, and the like. However, as compared to the primary sleep period, the score impact (e.g., impact on Sleep Score and Readiness Score) from naps may be relatively small, contributing on average between 0 and 10 points (out of a total 100 points) to the overall Sleep Score and Readiness Score. Moreover, if a pre-existing score (e.g., initial Sleep Score, initial Readiness Score) is relatively high, detected naps may have a relatively small effect on the overall scores (if any). For the average user, the changes introduced by nap detection may be relatively minor.

For example, referring to system 200, the ring may be worn by a user and may collect data associated with the user throughout a sleep day. The ring may collect data (e.g., temperature, heart rate, HRV) and transmit collected data to the mobile device. In some cases, the mobile device may forward (e.g., relay, transmit) the data received from the ring to the servers for processing. Additionally, or alternatively, the mobile device and/or the ring may perform processing on the collected data.

Continuing with the same example, the ring, the mobile device, the servers, or any combination thereof, may detect a supplemental sleep period (e.g., nap outside of a primary sleep period for the user that is longer than 15 minutes and shorter than 3 hours) based on the collected data. Upon detecting the nap, the servers may transmit an indication of the detected supplemental sleep period. Alternatively, in cases where the mobile device performs data processing, the mobile device may generate the indication of the detected supplemental sleep period. In this example, the next time the user opens the ring application, an indication of the detected supplemental sleep period may be presented to the user via the GUI of the mobile device. This may be further understood with reference to FIG. 4.

Figure 4:
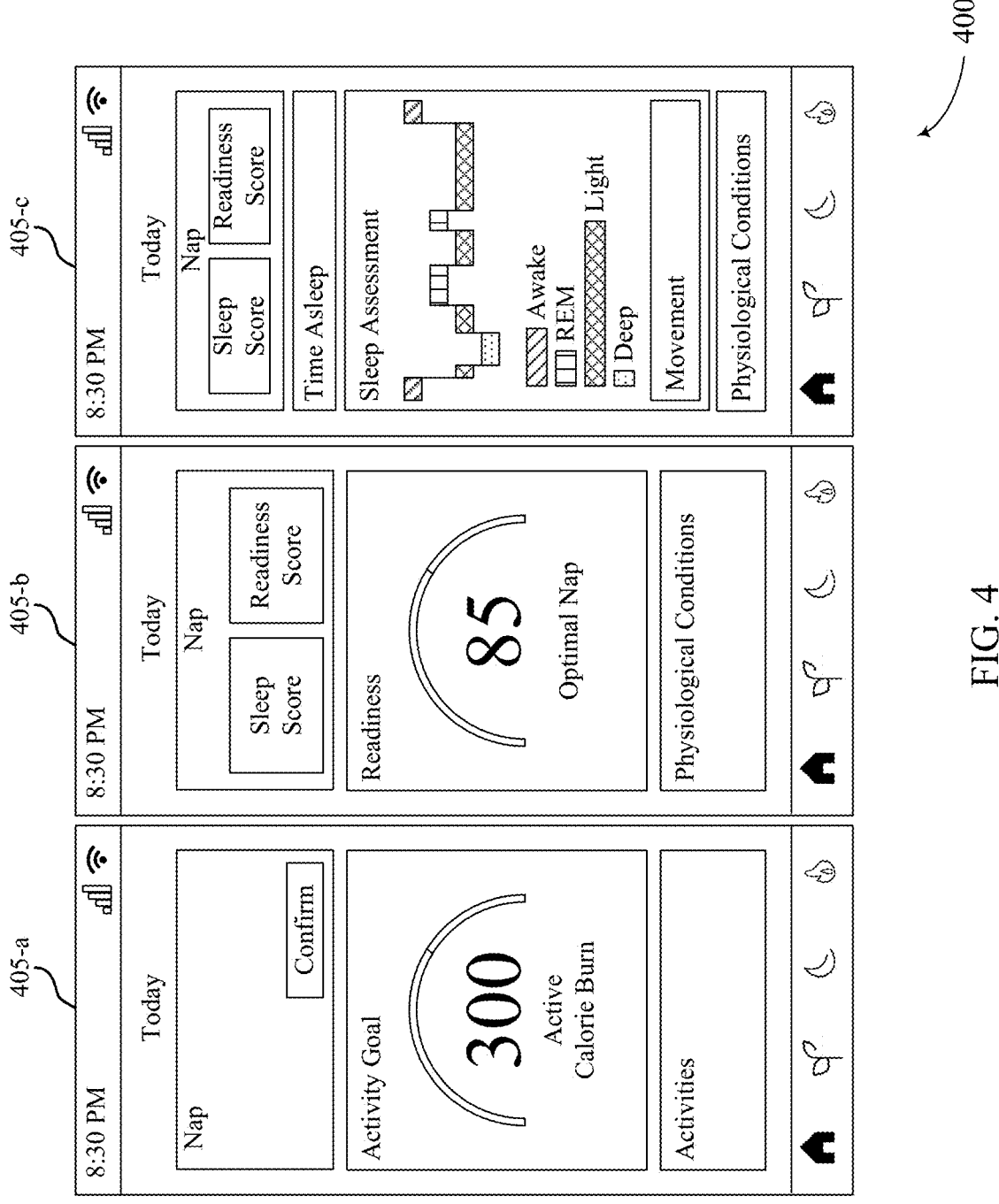
FIG. 4 illustrates an example of a graphical user interface (GUI) that supports a method and system for supplemental sleep detection in accordance with aspects of the present disclosure.

FIG. 4 illustrates an example of a GUI 400 that supports a method and system for supplemental sleep detection in accordance with aspects of the present disclosure. The GUI 400 may implement, or be implemented by, aspects of the system 100, system 200, timing diagram 300, or any combination thereof. For example, the GUI 400 may include an example of the GUI included within the mobile device illustrated in FIG. 4.

The GUI 400 illustrates a series of application pages 405 that may be displayed to the user via the GUI 400 (e.g., GUI illustrated in FIG. 2). Continuing with the example above, upon detecting a supplemental sleep period, the user may be presented with the application page 405-*a* upon opening the ring application. As shown in FIG. 4, the application page 405-*a* may display an indication that a supplemental sleep period was detected. The application page 405-*a* may indicate one or more parameters of the detected supplemental sleep period, including a time (e.g., time of day) that the supplemental sleep period was detected, a duration of the supplemental sleep period, and the like. Moreover, the application page 405-*a* may prompt the user to confirm or dismiss the nap (e.g., confirm/deny whether the system 200 correctly determined that the user took a nap). Additionally, in some implementations, the application page 405-*a* may display one or more scores (e.g., Sleep Score, Readiness Score) for the user for the respective sleep day.

In cases where the user dismisses the prompt on application page 405-*a*, the prompt may disappear, and the data from the (incorrectly) determined nap may not be used to update the user's Sleep Score and Readiness Score.

Conversely, upon confirming the supplemental sleep period on application page 405-*a*, the GUI 400 may display application page 405-*b*. In some cases, the user may only be able to confirm the nap within the sleep day during which the nap was detected. In other words, in some implementations, "unconfirmed" naps may not be confirmed/added the next sleep day. For example, in the event a detected nap goes unconfirmed before the end of the respective sleep day, the nap may be categorized as a "rest period," which may or may not be used to affect a user's Sleep Score or Readiness Score for that respective sleep day.

As shown in FIG. 4, the application page 405-*b* may display a "reward card" or "nap confirmation card" that indicates that the supplemental sleep period has been recorded. In some implementations, upon confirming that the nap (e.g., supplemental sleep period) is valid, the nap may be recorded/logged in an activity log for the user for the respective sleep day. Moreover, in some cases, the supplemental sleep period may be used to update (e.g., modify) one or more scores associated with the user (e.g., Sleep Score, Readiness Score). That is, data associated with the supplemental sleep period may be used to update the scores for the user for the respective sleep day during which the supplemental sleep period was detected. In some examples, the application page 405-*b* may display an indication of one or more supplemental sleep based insights (e.g., an indication of the quality of the supplemental sleep period) associated with the one or more updated scores. For example, the application page 405-*b* may display an updated Readiness Score based on a supplemental sleep period (e.g., nap) with a message indicating "optimal nap." By way of another example, the system may display an insight indicating whether the timing of the nap was beneficial or detrimental to the user's overall health, and may indicate how the user may better plan or time naps to optimize the health benefits of naps.

In some implementations, the system 200 may be configured to log, record, or otherwise recognize data associated with a detected supplemental sleep period without explicit confirmation from a user. For example, in some cases, the system 200 may identify a supplemental sleep period with a sufficient degree of precision, accuracy, or reliability (e.g., probability of a detected supplemental Sleep Score satisfying some threshold). In such cases, the system 200 may log or otherwise record the supplemental sleep period without displaying a prompt to a user and/or receiving an explicit confirmation from the user.

As noted previously herein, the mobile device and/or servers of the system 200 may be configured to record (e.g., store) and/or update scores associated with the user using the detected nap based on a timing of the nap relative to a primary sleep period for the respective day. In particular, if the nap is detected after the primary sleep period for the respective sleep day (e.g., after an initial Sleep Score and/or Readiness Score has been calculated based on the primary sleep period), the mobile device and/or server may be configured to update the initial Sleep Score and/or initial Readiness Score based on the data for the nap. Conversely, if the nap is detected before the primary sleep period for the respective sleep day (e.g., after an initial Sleep Score and/or Readiness Score has been calculated based on the primary sleep period), the ring, mobile device, and/or servers may store the data associated with the nap until the primary sleep period for the sleep day is detected. In this example, the mobile device and/or servers may be configured to wait until the primary sleep period for the sleep day is detected so that initial scores (e.g., initial Sleep Score, initial Readiness Score) may be calculated based on the primary sleep period. Subsequently, the initial scores may be updated based on the data for the nap.

Continuing with reference to FIG. 4, a user may be able to select the "reward card" or "nap confirmation card" on the application page 405-b in order to view details associated with the recorded nap, as shown in application page 405-c ("details modal"). In other words, tapping on the reward card shown on application page 405-b may cause the GUI 400 to display application page 405-c so that the user may quickly and easily view the impact of the nap. The application page 405-c may include a modal view including sleep details for the detected nap. For example, as shown in FIG. 4, the application page 405-c may illustrate details for the detected nap, including a duration of the nap, a timeline for the nap, a hypnogram of the nap (with nap start and end times as timestamps), intervals of different sleep stages (e.g., awake, REM sleep, light sleep, deep sleep) throughout the nap, a graph illustrating the user's movement throughout the nap, and the like. Additionally, or alternatively, the application page 405-c may display an effect of the nap on the user's scores (e.g., changes to Sleep Score and/or Readiness Score), and graphs of other biometric indicators throughout the nap (e.g., graph illustrating the user's heart rate throughout the course of the nap, graph illustrating the user's temperature throughout the course of the nap, graph illustrating the user's HRV throughout the course of the nap).

In some aspects, the GUI 400 may illustrate all sleep periods for a user within a given sleep day. All sleep periods may be accessible in "sleep" and "readiness" tabs that may be displayed via the GUI 400, where the user may be able to navigate between the different sleep periods within a sleep day using timestamps. In some cases, after confirming a nap, a user may be able to edit or delete the nap. For example, application page 405-c may enable the user to delete the nap, or modify characteristics of the nap. For instance, a user may be able to adjust a duration or time of the nap. Additionally, or alternatively, a user may be able to input (e.g., via the GUI of the mobile device) feedback regarding the nap. Feedback could include how the user feels after the nap (e.g., rested, rejuvenated, groggy, lethargic). Feedback could be input as narrative descriptions typed by the user, or via selections of pre-defined feedback options. In some implementations, the mobile device and/or the servers may be configured to utilize feedback entered by the user to determine the effect of naps, and to calculate updates to scores for the user.

In some aspects, data collected during detected and confirmed naps may be used to adjust one or more factors (e.g., contributors, contributing factors) that are used to determine a user's overall scores. For example, as noted previously herein, a user's overall Sleep Score may be calculated based on a set of contributors, including: total sleep, efficiency, restfulness, REM sleep, deep sleep, latency, timing, or any combination thereof. Similarly, a user's overall Readiness Score may be calculated based on a set of contributors, including: sleep, sleep balance, heart rate, HRV balance, recovery index, temperature, activity, activity balance, or any combination thereof. In this regard, after detecting/confirming a supplemental sleep period, the data from the supplemental sleep period may be used to update/modify at least a subset of the factors used to calculate the user's overall Sleep Score and Readiness Score.

For example, upon detecting/confirming a nap, the data from the nap may be used to update at least a subset of the factors for the Sleep Score (e.g., subset of total sleep, efficiency, restfulness, REM sleep, deep sleep, latency, timing). Subsequently, upon updating the subset of individual factors, the updated factors may be used to update the user's overall Sleep Score. By way of another example, the data from the nap may be used to update at least a subset of the factors for the Readiness Score (e.g., subset of sleep, sleep balance, heart rate, HRV balance, recovery index, temperature, activity, activity balance). Subsequently, upon updating the subset of individual factors, the updated factors may be used to update the user's overall Readiness Score. In some cases, there may be factors for the Sleep Score and/or Readiness Score that may not be affected by detected naps. For example, in some cases, the recovery index, latency, efficiency, activity, and/or activity balance factors may not be affected/updated by a detected nap.

In some implementations, both the changes to the user's overall Sleep Score and Readiness Score, as well as the changes to each of the respective contributing factors, may be displayed to the user via the application page 405-c. In other implementations, only the changes to the user's overall Sleep Score and Readiness Score as a result of the nap may be displayed, where the changes to the respective contributing factors may not be displayed, or highlighted. For example, in some cases, the application page 405-c may display the updated values for each of the contributing factors used to calculate the updated Sleep Score and Readiness Score, but may not display the previous contributing factors that were used prior to the nap. In other words, the application page 405-c may display the updated values for the contributing factors, but may not indicate how the nap changed the respective values.

As noted previously herein, naps may be beneficial to a user's overall health and sleep pattern. However, in some cases, depending on the relative timing and duration of a nap, the nap may actually have a detrimental effect on the user's overall health and sleep pattern. Accordingly, in some cases, the data from a detected/confirmed nap may have a positive or negative affect on each of the individual contributing factors, as well as the user's overall Sleep Score and Readiness Score. In other words, in some implementations, the data from the nap may increase or decrease (e.g., positive effect, detrimental effect, respectively) each of the individual factors, as well as the overall Sleep Score and Readiness Score.

However, "punishing" users for taking a nap by decreasing overall Sleep Score and Readiness Score may have a negative psychological impact on users, and may deter users from napping in the future when a nap may be beneficial. As such, in some implementations, the data from a detected/confirmed nap may only be used to increase overall Sleep Score and Readiness Score, but may not be used to decrease overall Sleep Score and Readiness Score. That is, if the nap improves the overall Sleep Score and Readiness Score, the improvements based on the nap may be implemented, and displayed to the user via application page 405-c. Conversely, in such implementations, if the nap has a negative impact on the overall Sleep Score and Readiness Score, the application page 405-c may simply illustrate no changes in the overall Sleep Score and Readiness Score. In other words, in some implementations, naps may only have positive (or zero) impact on overall Sleep Score and Readiness Score, and may not have a negative impact on overall Sleep Score and Readiness Score. As such, in some cases, naps cannot have an immediate negative effect, but in the long term too many or badly timed naps may start affecting Sleep Score and Readiness Score through the timing and efficiency contributors.

In implementations where naps may not be used to decrease overall Sleep Score and Readiness Score, the data from the nap may nonetheless be used to change (e.g., decrease) the individual contributing factors. However, the decreases to the individual factors may be "capped" at the point at which the impact on the overall Sleep Score and Readiness Score will have a negative effect. For example, in cases where a user takes a nap at a sub-optimal time, the "timing" contributing factor may decrease (e.g., negative impact), where the updated (e.g., decreased) timing factor may be displayed via application page 405-c. However, the mobile device and/or servers of the system 200 may be configured to cap, or limit, decreases to the individual contributing factors such that the updated contributing factors do not have a negative impact on the overall Sleep Score and Readiness Scores.

In some implementations, the mobile device and/or servers may generate alerts (e.g., messages, insights) associated with the nap that may be displayed to the user via the GUI 400 (e.g., application page 405-c). In particular, messages generated and displayed to the user via the GUI 400 may be associated with one or more characteristics (e.g., time of day, duration, success metric) of the detected nap. In some aspects, a "success metric" may indicate whether, or to what extent, the nap positively or negatively affected the user's overall Sleep Score and/or Readiness Score, individual contributors associated with the Sleep Score and Readiness Score, and the like. In particular, higher success metrics may indicate that the nap had an overall positive benefit to the user's health (e.g., net increase in Sleep Scores, Readiness Scores, individual contributing factors, or any combination thereof), whereas lower success metrics may indicate that the nap had a negligible or overall negative effect to the user's health (e.g., net decrease in Sleep Scores, Readiness Scores, individual contributing factors, or any combination thereof). In this regard, the system 200 may be configured to display messages/insights to the user in order to facilitate effective, healthy napping patterns for the user. Additionally, messages generated and displayed to the user via the GUI 400 may request feedback for the detected nap. For example, the message may include a request for user feedback associated with how rested the user feels, or if the user feels groggy or tired following the nap.

In some cases, the system 200 may use physiological data associated with a nap, user feedback associated with a nap, or both, to determine optimal nap information/parameters for a user (e.g., an optimal nap duration, an optimal nap time, an optimal nap environment, or the like thereof). For example, a user may take an hour long nap and report feeling rested upon waking up from the nap. A ring associated with the user may also detect that the user experienced an average heart rate associated with deeper sleep during the nap. As such, the system 200 may determine that an hour long nap may be an optimal nap duration for the user. In some cases, the optimal nap information/parameters for a user may be based on trends associated with naps (e.g., with data associated with multiple naps detected or reported by a user). Additionally or alternatively, the optimal nap information may include optimal nap information associated with various scenarios. For example, a first set of optimal nap information/parameters may be associated with a user taking a nap prior to experiencing a decrease in sleep quality (e.g., a decrease in Sleep Score) and a second set of optimal nap information/parameters may be associated with a user taking a nap after experiencing a decrease in sleep quality.

For example, a server of the system 200 may cause the mobile device to display a message (e.g., insight) that informs the user as to whether the timing of the nap is expected to have a positive/negative impact, whether the duration of the nap is expected to have a positive/negative impact, and the like (e.g., based on optimal nap information associated with the user). In some cases, the messages displayed to the user via the GUI of the mobile device may indicate how the nap affected the overall scores (e.g., overall Sleep Score, overall Readiness Score) and/or the individual contributing factors. For example, a message may indicate "Your nap improved your Readiness Score, nice going! What type of activity would help you stay focused for the rest of the day?"

In cases where the timing/duration of the nap was not optimal, the messages may provide suggestions for the user to change their napping patterns in order to improve their overall sleep patterns and general health. For example, the message may indicate "You gave your body a nice break! Keep taking it easy for the rest of the day, but try to avoid extra naps so that you're ready for a good night's sleep," or "How are you feeling after your naps? Sometimes we need all the downtime we can get, but try to resist napping too close to bedtime to make sure that you're ready for the most important sleep period of the day."

In some cases, the mobile device and/or servers may generate alerts associated with a suggested nap (e.g., suggested nap schedule) that may be displayed to the user via the GUI 400 (e.g., based on optimal nap information associated with the user). In some examples, components of the system 200 may collect data from external sources (e.g., additional apps) for use in evaluation of sleep patterns for a user. For example, components of the system 200 may collect data associated with scheduled events of the user (e.g., from a calendar app) and may determine that a scheduled event may impact the sleep pattern of the user (e.g., impact the Readiness Score, the Sleep Score). In some cases, the system 200 may determine impacts to the sleep pattern of the user based on a circadian rhythm of the user (e.g., based on chronotypes of the user). In such cases, the system 200 may determine that a nap may reduce impacts of the scheduled event on the sleep pattern of the user and may determine an optimal time and duration associated with a suggested nap (e.g., based on a circadian rhythm of the user, sleep patterns of the user, data associated with previous naps, feedback the user has provided following previous naps, optimal nap information/parameters associated with the user, or the like). A server of the system 200 may cause the mobile device to display a message indicating a nap suggestion and parameters associated with the suggested nap. As an illustrative example, components of the system 200 may identify that a user typically goes to bed around 9:30 pm but has an event scheduled until 11:00 pm on a given day. The system 200 may determine that an hour nap taken at 3:00 pm the day of the event may reduce impacts (e.g., to overall Sleep Score, to overall Readiness Score) of the delayed bedtime. As such, a server of the system 200 may cause the mobile device to display a message to the user via the GUI 400 indicating the nap suggestion.

In another example, the system 200 may suggest a nap to the user based on a previous sleep period (e.g., a primary sleep period) or feedback received from the user associated with a previous sleep period. For example, the system 200 may identify that a previous primary sleep period was interrupted multiple times (e.g., the user woke up many times) and that the user indicated that they did not feel rested upon waking up from the previous sleep period. In such cases, the system 200 may determine that a nap may reduce negative impacts (e.g., a decrease in Readiness Score) due to the previous primary sleep period and may determine an optimal time and duration associated with the suggested nap. Further, the system 200 may cause the mobile device to display a message to the user via the GUI 400 indicating the nap suggestion.

Additionally or alternatively, components of the system 200 may suggest naps based on data associated with previous naps. For example, the system 200 may identify that a user is experiencing a degraded Readiness Score (e.g., a Readiness Score lower than an average Readiness Score for the user). Additionally, the system 200 may identify that a nap may improve the Readiness Score of the user based on data associated with previous naps (e.g., nap schedules). In such cases, a server of the system 200 may cause the mobile device to display a message indicating a nap suggestion and parameters associated with the suggested nap to the user. As an illustrative example, the system 200 may identify that a user is experiencing a degraded Readiness Score and that hour long naps taken between the hours of 2:00 pm and 4:00 pm typically improve the Readiness Score of the user by 5 points (e.g., based on optimal nap information/parameters associated with the user). As such, a server of the system 200 may cause the mobile device to display a message to the user suggesting that the user take an hour long nap between the hours of 2:00 pm and 4:00 pm.

In some aspects, the system 200 may be configured to suggest that a user take a nap. For example, the system 200 may identify that the user could benefit from a nap based on parameters or characteristics associated with the user (e.g., the user's Sleep Score, the user's Readiness Score, optimal nap information/parameters associated with the user), and may provide an alert to the user (e.g., via the user device 106) to suggest that the user take a nap. In some cases, the system 200 may suggest certain characteristics associated with the recommended nap, such as a suggested time of the nap, a suggested nap duration, etc. In some cases, the system 200 may utilize other detected physiological parameters and/or historical data associated with the user to know when the user has benefitted from naps in the past under similar circumstances, and use such to suggest both a time and a duration for a suggested nap.

In some implementations, the system 200 may be configured to display (e.g., via the user device 106) optimal nap information/parameters associated with the user. For example, the GUI 275 of the user device 106 may display information associated with naps the user has taken in the past so that the user is able to see what nap duration and/or nap timing has been most optimal for the user. Moreover, the system 200 may display information regarding physiological conditions (e.g., levels of fatigue, Sleep/Readiness scores, elevated heart rate, etc.) associated with the user have led to the most benefit from a nap, as compared to physiological conditions which may not significantly benefit from a nap. Stated differently, the system 200 may display information that indicates a user may significantly benefit from a nap under a first set of conditions, but may not significantly benefit from a nap under a second set of conditions. As such, the system 200 may provide insights as to when a user should consider taking a nap.

Figure 5:
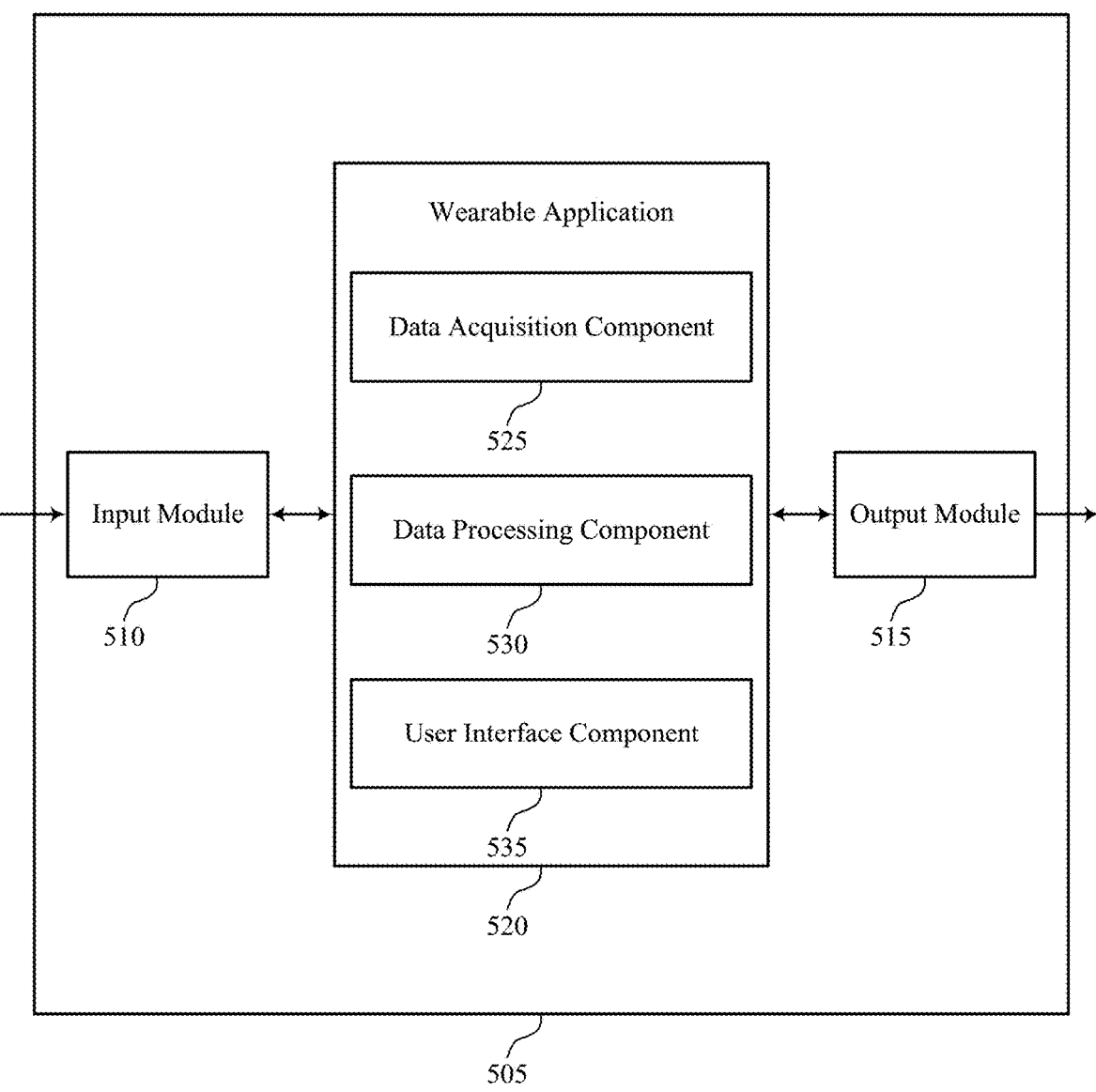
FIG. 5 shows a block diagram of an apparatus that supports a method and system for supplemental sleep detection in accordance with aspects of the present disclosure.

FIG. 5 shows a block diagram 500 of a device 505 that supports a method and system for supplemental sleep detection in accordance with aspects of the present disclosure. In some aspects, the device 505 may include an example of a mobile device, as illustrated in FIGS. 1 and 2. The device 505 may include an input module 510, an output module 515, and a wearable application 520. The device 505 may also include a processor. Each of these components may be in communication with one another (e.g., via one or more buses).

The input module 510 may manage input signals for the device 505. For example, the input module 510 may identify input signals based on an interaction with a wearable device (e.g., ring), modem, a keyboard, a mouse, a touchscreen, or a similar device. These input signals may be associated with user input or processing at other components or devices. In some cases, the input module 510 may utilize an operating system such as iOS®, ANDROID®, MS-DOS®, MS-WINDOWS®, OS/2®, UNIX®, LINUX®, or another known operating system to handle input signals. The input module 510 may send aspects of these input signals to other components of the device 505 for processing. For example, the input module 510 may transmit input signals to the wearable application 520 to support a method and system for supplemental sleep detection. In some cases, the input module 510 may be a component of an I/O controller 710 as described with reference to FIG. 7.

The output module 515 may manage output signals for the device 505. For example, the output module 515 may receive signals from other components of the device 505, such as the wearable application 520 or servers, and may transmit these signals to other components or devices (e.g., wearable device, servers). In some examples, the output module 515 may transmit output signals for display in a user interface, for storage in a database or data store, for further processing at a server or server cluster, or for any other processes at any number of devices or systems. In some cases, the output module 515 may be a component of an I/O controller 710 as described with reference to FIG. 7.

For example, the wearable application 520 may include a data acquisition component 525, a data processing component 530, a user interface component 535, or any combination thereof. In some examples, the wearable application 520, or various components thereof, may be configured to perform various operations (e.g., receiving, monitoring, transmitting) using or otherwise in cooperation with the input module 510, the output module 515, or both. For example, the wearable application 520 may receive information from the input module 510, send information to the output module 515, or be integrated in combination with the input module 510, the output module 515, or both to receive information, transmit information, or perform various other operations as described herein.

The wearable application 520 may support supplemental sleep detection in accordance with examples as disclosed herein. The data acquisition component 525 may be configured as or otherwise support a means for receiving data associated with a user from a wearable device. The data processing component 530 may be configured as or otherwise support a means for detecting a primary sleep period for the user based at least in part on the received data. The data processing component 530 may be configured as or otherwise support a means for detecting a supplemental sleep period based at least in part on the received data. The user interface component 535 may be configured as or otherwise support a means for causing a GUI of a user device to display an indication of the detected supplemental sleep period. The user interface component 535 may be configured as or otherwise support a means for receiving, via the user device and in response to the indication of the detected supplemental sleep period, a confirmation of the supplemental sleep period. The data processing component 530 may be configured as or otherwise support a means for generating, based at least in part on the confirmation, one or more insights associated with the user based at least in part on the primary sleep period and the supplemental sleep period.

Figure 6:
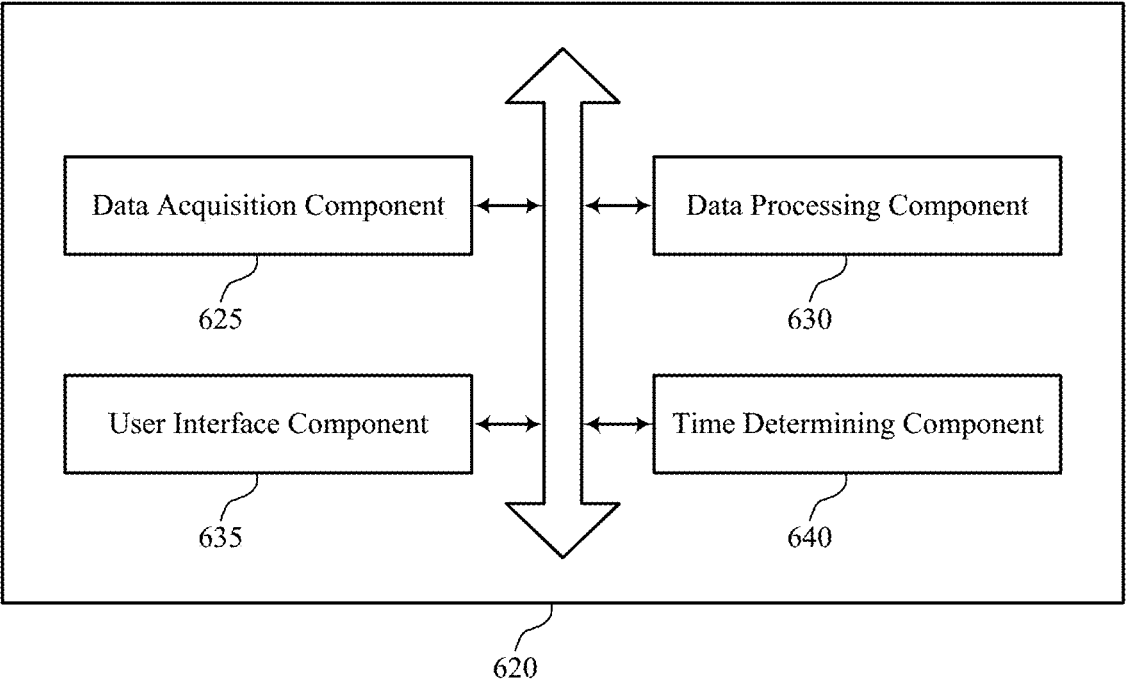
FIG. 6 shows a block diagram of a wearable application that supports a method and system for supplemental sleep detection in accordance with aspects of the present disclosure.

FIG. 6 shows a block diagram 600 of a wearable application 620 that supports a method and system for supplemental sleep detection in accordance with aspects of the present disclosure. Wearable application 620 may be an example of aspects of a wearable application 520, as described herein. The wearable application 620, or various components thereof, may be an example of means for performing various aspects of a method and system for supplemental sleep detection as described herein. For example, the wearable application 620 may include a data acquisition component 625, a data processing component 630, a user interface component 635, a time determining component 640, or any combination thereof. Each of these components may communicate, directly or indirectly, with one another (e.g., via one or more buses).

The wearable application 620 may support supplemental sleep detection in accordance with examples as disclosed herein. The data acquisition component 625 may be configured as or otherwise support a means for receiving data associated with a user from a wearable device. The data processing component 630 may be configured as or otherwise support a means for detecting a primary sleep period for the user based at least in part on the received data. In some examples, the data processing component 630 may be configured as or otherwise support a means for detecting a supplemental sleep period based at least in part on the received data. The user interface component 635 may be configured as or otherwise support a means for causing a GUI of a user device to display an indication of the detected supplemental sleep period. In some examples, the user interface component 635 may be configured as or otherwise support a means for receiving, via the user device and in response to the indication of the detected supplemental sleep period, a confirmation of the supplemental sleep period. In some examples, the data processing component 630 may be configured as or otherwise support a means for generating, based at least in part on the confirmation, one or more insights associated with the user based at least in part on the primary sleep period and the supplemental sleep period.

In some examples, the data processing component 630 may be configured as or otherwise support a means for determining one or more scores based at least in part on the primary sleep period. In some examples, the data processing component 630 may be configured as or otherwise support a means for updating the one or more scores based at least in part on the supplemental sleep period.

In some examples, to support updating the one or more scores, the data acquisition component 625 may be configured as or otherwise support a means for updating at least a subset of factors of the set of factors.

In some examples, the time determining component 640 may be configured as or otherwise support a means for identifying a time of day that the supplemental sleep period occurred, wherein generating the one or more insights is based at least in part on whether the time of day occurs before or after a configured cut-off time.

In some examples, to support generating the one or more insights, the time determining component 640 may be configured as or otherwise support a means for updating a first set of one or more scores associated with a first sleep day for the user based at least in part on the time of day being prior to the configured cut-off time. In some examples, to support generating the one or more insights, the time determining component 640 may be configured as or otherwise support a means for updating a second set of one or more scores associated with a second sleep day for the user based at least in part on the time of day being subsequent to the configured cut-off time.

In some examples, the user interface component 635 may be configured as or otherwise support a means for causing the GUI of the user device to display a message associated with one or more characteristics of the detected supplemental sleep period. In some examples, the one or more characteristics comprise a time of day that the supplemental sleep period was detected, a duration of the supplemental sleep period, a success metric associated with the supplemental sleep period, or any combination thereof. In some examples, the one or more insights comprise a Sleep Score, a Readiness Score, or both.

Figure 7:
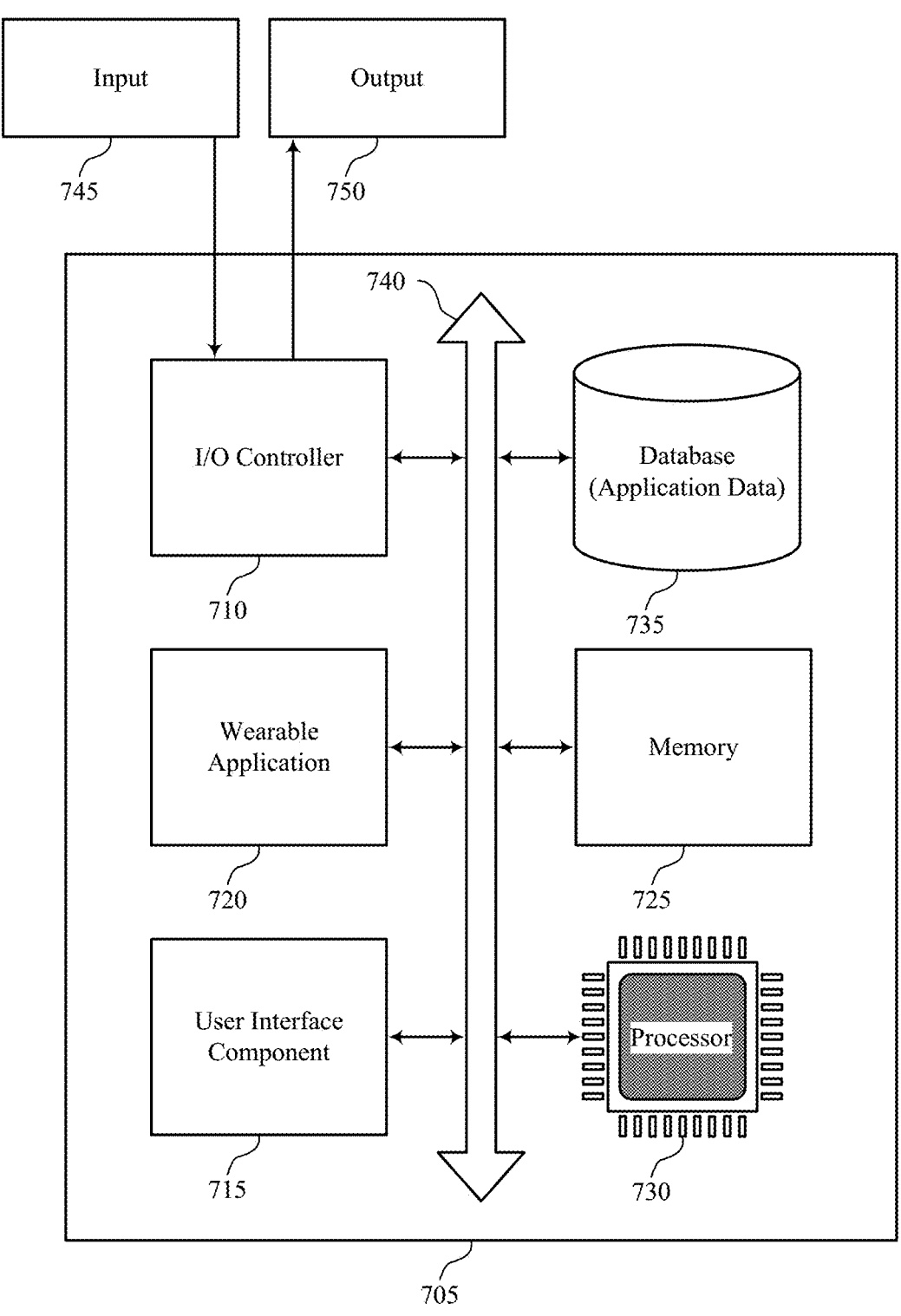
FIG. 7 shows a diagram of a system including a device that supports a method and system for supplemental sleep detection in accordance with aspects of the present disclosure.

FIG. 7 shows a diagram of a system 700 including a device 705 that supports a method and system for supplemental sleep detection in accordance with aspects of the present disclosure. The device 705 may be an example of or include the components of a device 505 as described herein. In this regard, the device 705 may include an example of a mobile device shown and described in FIGS. 1 and 2. The device 705 may include components for bi-directional data communications including components for transmitting and receiving communications, such as a wearable application 720, an I/O controller 710, a user interface component 715, a memory 725, a processor 730, and a database 735. These components may be in electronic communication or otherwise coupled (e.g., operatively, communicatively, functionally, electronically, electrically) via one or more buses (e.g., a bus 740).

The I/O controller 710 may manage input signals 745 and output signals 750 for the device 705. The I/O controller may include an example of the communication module of the mobile device shown and described in FIG. 2. In this regard, the input signals 745 and output signals 750 may illustrate signaling exchanged between the mobile device and the ring, and the mobile device and the servers, as illustrated in FIG. 2. The I/O controller 710 may also manage peripherals not integrated into the device 705. In some cases, the I/O controller 710 may represent a physical connection or port to an external peripheral. In some cases, the I/O controller 710 may utilize an operating system such as iOS®, ANDROID®, MS-DOS®, MS-WINDOWS®, OS/2®, UNIX®, LINUX®, or another known operating system. In other cases, the I/O controller 710 may represent or interact with a wearable device (e.g., ring), modem, a keyboard, a mouse, a touchscreen, or a similar device. In some cases, the I/O controller 710 may be implemented as part of a processor 730. In some examples, a user may interact with the device 705 via the I/O controller 710 or via hardware components controlled by the I/O controller 710.

The user interface component 715 may manage data storage and processing in a database 735. In some cases, a user may interact with the user interface component 715. In other cases, the user interface component 715 may operate automatically without user interaction. The database 735 may be an example of a single database, a distributed database, multiple distributed databases, a data store, a data lake, or an emergency backup database.

Memory 725 may include RAM and ROM. The memory 725 may store computer-readable, computer-executable software including instructions that, when executed, cause the processor 730 to perform various functions described herein. In some cases, the memory 725 may contain, among other things, a basic I/O system (BIOS) which may control basic hardware or software operation such as the interaction with peripheral components or devices.

The processor 730 may include an intelligent hardware device, (e.g., a general-purpose processor, a digital signal processor (DSP), a central processing unit (CPU), a micro-controller, an application-specific integrated circuit (ASIC), a field-programmable gate array (FPGA), a programmable logic device, a discrete gate or transistor logic component, a discrete hardware component, or any combination thereof). In some cases, the processor 730 may be configured to operate a memory array using a memory controller. In other cases, a memory controller may be integrated into the processor 730. The processor 730 may be configured to execute computer-readable instructions stored in a memory 725 to perform various functions (e.g., functions or tasks supporting a method and system for supplemental sleep detection).

The wearable application 720 may support supplemental sleep detection in accordance with examples as disclosed herein. For example, the wearable application 720 may be configured as or otherwise support a means for receiving data associated with a user from a wearable device. The wearable application 720 may be configured as or otherwise support a means for detecting a primary sleep period for the user based at least in part on the received data. The wearable application 720 may be configured as or otherwise support a means for detecting a supplemental sleep period based at least in part on the received data. The wearable application 720 may be configured as or otherwise support a means for causing a GUI of a user device to display an indication of the detected supplemental sleep period. The wearable application 720 may be configured as or otherwise support a means for receiving, via the user device and in response to the indication of the detected supplemental sleep period, a confirmation of the supplemental sleep period. The wearable application 720 may be configured as or otherwise support a means for generating, based at least in part on the confirmation, one or more insights associated with the user based at least in part on the primary sleep period and the supplemental sleep period.

By including or configuring the wearable application 720 in accordance with examples as described herein, the device 705 may support techniques for improved sleep tracking using data collected by a wearable device. In particular, techniques described herein may be used to detect multiple sleep periods for a given user, including primary sleep periods and naps, that may be used to generate more accurate and comprehensive scores (e.g., Sleep Scores, Readiness Scores) for the user. By providing a user with a more comprehensive evaluation of their sleep patterns, techniques described herein may enable the user to effectively adjust their sleep patterns, which may improve the sleep quality and overall health for the user.

FIG. 8 shows a flowchart illustrating a method 800 that supports a method and system for supplemental sleep detection in accordance with aspects of the present disclosure. The operations of the method 800 may be implemented by a user device (e.g., mobile device) or its components as described herein. For example, the operations of the method 800 may be performed by a mobile device as described with reference to FIGS. 1 through 7. In some examples, a mobile device may execute a set of instructions to control the functional elements of the mobile device to perform the described functions. Additionally or alternatively, the mobile device may perform aspects of the described functions using special-purpose hardware.

At 805, the method may include receiving data associated with a user from a wearable device. The operations of 805 may be performed in accordance with examples as disclosed herein. In some examples, aspects of the operations of 805 may be performed by a data acquisition component 625 as described with reference to FIG. 6.

At 810, the method may include detecting a primary sleep period for the user based at least in part on the received data. The operations of 810 may be performed in accordance with examples as disclosed herein. In some examples, aspects of the operations of 810 may be performed by a data processing component 630 as described with reference to FIG. 6.

At 815, the method may include detecting a supplemental sleep period based at least in part on the received data. The operations of 815 may be performed in accordance with examples as disclosed herein. In some examples, aspects of the operations of 815 may be performed by a data processing component 630 as described with reference to FIG. 6.

At 820, the method may include causing a GUI of a user device (e.g., mobile device) to display an indication of the detected supplemental sleep period. The operations of 820 may be performed in accordance with examples as disclosed herein. In some examples, aspects of the operations of 820 may be performed by a user interface component 635 as described with reference to FIG. 6.

At 825, the method may include receiving, via the user device (e.g., mobile device) and in response to the indication of the detected supplemental sleep period, a confirmation of the supplemental sleep period. The operations of 825 may be performed in accordance with examples as disclosed herein. In some examples, aspects of the operations of 825 may be performed by a user interface component 635 as described with reference to FIG. 6.

At 830, the method may include generating, based at least in part on the confirmation, one or more insights associated with the user based at least in part on the primary sleep period and the supplemental sleep period. The operations of 830 may be performed in accordance with examples as disclosed herein. In some examples, aspects of the operations of 830 may be performed by a data processing component 630 as described with reference to FIG. 6.

FIG. 9 shows a flowchart illustrating a method 900 that supports a method and system for supplemental sleep detection in accordance with aspects of the present disclosure. The operations of the method 900 may be implemented by a user device (e.g., mobile device) or its components as described herein. For example, the operations of the method 900 may be performed by a mobile device as described with reference to FIGS. 1 through 7. In some examples, a mobile device may execute a set of instructions to control the functional elements of the mobile device to perform the described functions. Additionally or alternatively, the mobile device may perform aspects of the described functions using special-purpose hardware.

At 905, the method may include receiving data associated with a user from a wearable device. The operations of 905 may be performed in accordance with examples as disclosed herein. In some examples, aspects of the operations of 905 may be performed by a data acquisition component 625 as described with reference to FIG. 6.

At 910, the method may include detecting a primary sleep period for the user based at least in part on the received data. The operations of 910 may be performed in accordance with examples as disclosed herein. In some examples, aspects of the operations of 910 may be performed by a data processing component 630 as described with reference to FIG. 6.

At 915, the method may include detecting a supplemental sleep period based at least in part on the received data. The operations of 915 may be performed in accordance with examples as disclosed herein. In some examples, aspects of the operations of 915 may be performed by a data processing component 630 as described with reference to FIG. 6.

At 920, the method may include causing a GUI of a user device (e.g., mobile device) to display an indication of the detected supplemental sleep period. The operations of 920 may be performed in accordance with examples as disclosed herein. In some examples, aspects of the operations of 920 may be performed by a user interface component 635 as described with reference to FIG. 6.

At 925, the method may include receiving, via the user device (e.g., mobile device) and in response to the indication of the detected supplemental sleep period, a confirmation of the supplemental sleep period. The operations of 925 may be performed in accordance with examples as disclosed herein. In some examples, aspects of the operations of 925 may be performed by a user interface component 635 as described with reference to FIG. 6.

At 930, the method may include determining one or more scores based at least in part on the primary sleep period. The operations of 930 may be performed in accordance with examples as disclosed herein. In some examples, aspects of the operations of 930 may be performed by a data processing component 630 as described with reference to FIG. 6.

At 935, the method may include updating the one or more scores based at least in part on the supplemental sleep period. The operations of 935 may be performed in accordance with examples as disclosed herein. In some examples, aspects of the operations of 935 may be performed by a data processing component 630 as described with reference to FIG. 6.

Figure 10:
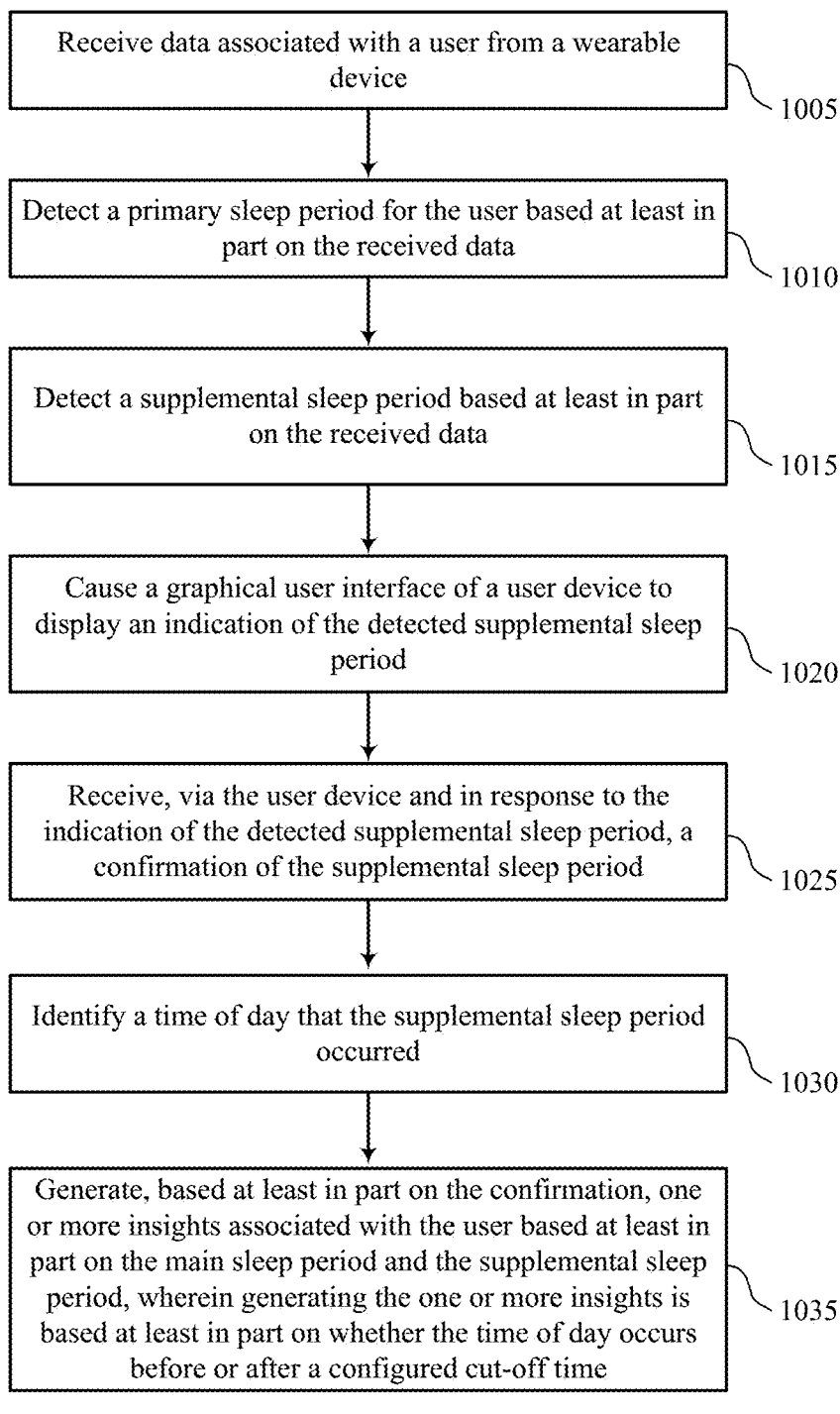

FIG. 10 shows a flowchart illustrating a method 1000 that supports a method and system for supplemental sleep detection in accordance with aspects of the present disclosure. The operations of the method 1000 may be implemented by a user device (e.g., mobile device) or its components as described herein. For example, the operations of the method 1000 may be performed by a mobile device as described with reference to FIGS. 1 through 7. In some examples, a mobile device may execute a set of instructions to control the functional elements of the mobile device to perform the described functions. Additionally or alternatively, the mobile device may perform aspects of the described functions using special-purpose hardware.

At 1005, the method may include receiving data associated with a user from a wearable device. The operations of 1005 may be performed in accordance with examples as disclosed herein. In some examples, aspects of the operations of 1005 may be performed by a data acquisition component 625 as described with reference to FIG. 6.

At 1010, the method may include detecting a primary sleep period for the user based at least in part on the received data. The operations of 1010 may be performed in accordance with examples as disclosed herein. In some examples, aspects of the operations of 1010 may be performed by a data processing component 630 as described with reference to FIG. 6.

At 1015, the method may include detecting a supplemental sleep period based at least in part on the received data. The operations of 1015 may be performed in accordance with examples as disclosed herein. In some examples, aspects of the operations of 1015 may be performed by a data processing component 630 as described with reference to FIG. 6.

At 1020, the method may include causing a GUI of a user device (e.g., mobile device) to display an indication of the detected supplemental sleep period. The operations of 1020 may be performed in accordance with examples as disclosed herein. In some examples, aspects of the operations of 1020 may be performed by a user interface component 635 as described with reference to FIG. 6.

At 1025, the method may include receiving, via the user device (e.g., mobile device) and in response to the indication of the detected supplemental sleep period, a confirmation of the supplemental sleep period. The operations of 1025 may be performed in accordance with examples as disclosed herein. In some examples, aspects of the operations of 1025 may be performed by a user interface component 635 as described with reference to FIG. 6.

At 1030, the method may include identifying a time of day that the supplemental sleep period occurred. The operations of 1030 may be performed in accordance with examples as disclosed herein. In some examples, aspects of the operations of 1030 may be performed by a time determining component 640 as described with reference to FIG. 6.

At 1035, the method may include generating, based at least in part on the confirmation, the one or more insights associated with the user based at least in part on the primary sleep period and the supplemental sleep period, and based at least in part on whether the time of day occurs before or after a configured cut-off time. The operations of 1035 may be performed in accordance with examples as disclosed herein. In some examples, aspects of the operations of 1035 may be performed by a data processing component 630 as described with reference to FIG. 6.

FIG. 11 shows a flowchart illustrating a method 1100 that supports a method and system for supplemental sleep detection in accordance with aspects of the present disclosure. The operations of the method 1100 may be implemented by a user device (e.g., mobile device) or its components as described herein. For example, the operations of the method 1100 may be performed by a mobile device as described with reference to FIGS. 1 through 7. In some examples, a mobile device may execute a set of instructions to control the functional elements of the mobile device to perform the described functions. Additionally or alternatively, the mobile device may perform aspects of the described functions using special-purpose hardware.

At 1105, the method may include receiving data associated with a user from a wearable device. The operations of 1105 may be performed in accordance with examples as disclosed herein. In some examples, aspects of the operations of 1105 may be performed by a data acquisition component 625 as described with reference to FIG. 6.

At 1110, the method may include detecting a primary sleep period for the user based at least in part on the received data. The operations of 1110 may be performed in accordance with examples as disclosed herein. In some examples, aspects of the operations of 1110 may be performed by a data processing component 630 as described with reference to FIG. 6.

At 1115, the method may include detecting a supplemental sleep period based at least in part on the received data. The operations of 1115 may be performed in accordance with examples as disclosed herein. In some examples, aspects of the operations of 1115 may be performed by a data processing component 630 as described with reference to FIG. 6.

At 1120, the method may include causing a GUI of a user device (e.g. mobile device) to display an indication of the detected supplemental sleep period. The operations of 1120 may be performed in accordance with examples as disclosed herein. In some examples, aspects of the operations of 1120 may be performed by a user interface component 635 as described with reference to FIG. 6.

At 1125, the method may include receiving, via the user device (e.g., mobile device) and in response to the indication of the detected supplemental sleep period, a confirmation of the supplemental sleep period. The operations of 1125 may be performed in accordance with examples as disclosed herein. In some examples, aspects of the operations of 1125 may be performed by a user interface component 635 as described with reference to FIG. 6.

At 1130, the method may include generating, based at least in part on the confirmation, one or more insights associated with the user based at least in part on the primary sleep period and the supplemental sleep period. The operations of 1130 may be performed in accordance with examples as disclosed herein. In some examples, aspects of the operations of 1130 may be performed by a data processing component 630 as described with reference to FIG. 6.

At 1135, the method may include causing the GUI of the user device to display a message associated with one or more characteristics of the detected supplemental sleep period. The operations of 1135 may be performed in accordance with examples as disclosed herein. In some examples, aspects of the operations of 1135 may be performed by a user interface component 635 as described with reference to FIG. 6.

A method for supplemental sleep detection is described. The method may include receiving data associated with a user from a wearable device, detecting a primary sleep period for the user based at least in part on the received data, detecting a supplemental sleep period based at least in part on the received data, causing a GUI of a user device to display an indication of the detected supplemental sleep period, receiving, via the user device and in response to the indication of the detected supplemental sleep period, a confirmation of the supplemental sleep period, and generating, based at least in part on the confirmation, one or more insights associated with the user based at least in part on the primary sleep period and the supplemental sleep period.

An apparatus for supplemental sleep detection is described. The apparatus may include a processor, memory coupled with the processor, and instructions stored in the memory. The instructions may be executable by the processor to cause the apparatus to receive data associated with a user from a wearable device, detect a primary sleep period for the user based at least in part on the received data, detect a supplemental sleep period based at least in part on the received data, cause a GUI of a user device to display an indication of the detected supplemental sleep period, receive, via the user device and in response to the indication of the detected supplemental sleep period, a confirmation of the supplemental sleep period, and generate, based at least in part on the confirmation, one or more insights associated with the user based at least in part on the primary sleep period and the supplemental sleep period.

Another apparatus for supplemental sleep detection is described. The apparatus may include means for receiving data associated with a user from a wearable device, means for detecting a primary sleep period for the user based at least in part on the received data, means for detecting a supplemental sleep period based at least in part on the received data, means for causing a GUI of a user device to display an indication of the detected supplemental sleep period, means for receiving, via the user device and in response to the indication of the detected supplemental sleep period, a confirmation of the supplemental sleep period, and means for generating, based at least in part on the confirmation, one or more insights associated with the user based at least in part on the primary sleep period and the supplemental sleep period.

A non-transitory computer-readable medium storing code for supplemental sleep detection is described. The code may include instructions executable by a processor to receive data associated with a user from a wearable device, detect a primary sleep period for the user based at least in part on the received data, detect a supplemental sleep period based at least in part on the received data, cause a GUI of a user device to display an indication of the detected supplemental sleep period, receive, via the user device and in response to the indication of the detected supplemental sleep period, a confirmation of the supplemental sleep period, and generate, based at least in part on the confirmation, one or more insights associated with the user based at least in part on the primary sleep period and the supplemental sleep period.

Some examples of the method, apparatuses, and non-transitory computer-readable medium described herein may further include operations, features, means, or instructions for determining one or more scores based at least in part on the primary sleep period and updating the one or more scores based at least in part on the supplemental sleep period.

In some examples of the method, apparatuses, and non-transitory computer-readable medium described herein, updating the one or more scores may include operations, features, means, or instructions for updating at least a subset of factors of the set of factors.

Some examples of the method, apparatuses, and non-transitory computer-readable medium described herein may further include operations, features, means, or instructions for identifying a time of day that the supplemental sleep period occurred, wherein updating the one or more scores may be based at least in part on whether the time of day occurs before or after a configured cut-off time.

In some examples of the method, apparatuses, and non-transitory computer-readable medium described herein, generating the one or more insights may include operations, features, means, or instructions for updating a first set of one or more scores associated with a first sleep day for the user based at least in part on the time of day being prior to the configured cut-off time and updating a second set of one or more scores associated with a second sleep day for the user based at least in part on the time of day being subsequent to the configured cut-off time.

Some examples of the method, apparatuses, and non-transitory computer-readable medium described herein may further include operations, features, means, or instructions for causing the GUI of the user device to display a message associated with one or more characteristics of the detected supplemental sleep period.

In some examples of the method, apparatuses, and non-transitory computer-readable medium described herein, the one or more characteristics comprise a time of day that the supplemental sleep period was detected, a duration of the supplemental sleep period, a success metric associated with the supplemental sleep period, or any combination thereof.

In some examples of the method, apparatuses, and non-transitory computer-readable medium described herein, the one or more insights comprise a Sleep Score, a Readiness Score, or both.

It should be noted that the methods described above describe possible implementations, and that the operations and the steps may be rearranged or otherwise modified and that other implementations are possible. Furthermore, aspects from two or more of the methods may be combined.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A system for supplemental sleep detection, comprising:
a wearable device comprising one or more sensors configured to acquire physiological data from a user;
a user device communicatively coupled with the wearable device; and
one or more processors communicatively coupled with the user device, the wearable device, or both, wherein the one or more processors are configured to:
    receive, from the wearable device, physiological data acquired from the user via the wearable device;
    detect a primary sleep period for the user during a sleep day based at least in part on a first subset of the physiological data, wherein the sleep day ends at a determined cut-off time of day;
    generate a set of one or more scores associated with the sleep day based at least in part on the primary sleep period;
    detect a supplemental sleep period based at least in part on a second subset of the physiological data;
    identify a time of day that the supplemental sleep period occurred;
    update the set of one or more scores associated with the sleep day to generate an updated set of one or more scores based at least in part on the supplemental sleep period and based at least in part on the time of day associated with the supplemental sleep period occurring before the determined cut-off time of day;
    generate one or more signals to cause a graphical user interface (GUI) of the user device associated with the wearable device to display the updated set of one or more scores after the supplemental sleep period and an indication of supplemental sleep period; and
    receive, via the user device and in response to the indication of the supplemental sleep period, a confirmation of the supplemental sleep period.

2. The system of claim 1, wherein the determined cut-off time of day is based at least in part on a time of day that the user typically begins a primary sleep period each calendar day.

3. The system of claim 1, wherein the determined cut-off time of day is based at least in part on a sleeping pattern of the user.

4. The system of claim 1, wherein the determined cut-off time of day is associated with the user beginning a second primary sleep period associated with a second sleep day.

5. The system of claim 1, wherein the sleep day aligns with a calendar day such that determined cut-off time of day is midnight.

6. The system of claim 1, wherein the one or more processors are further configured to:
receive, via the user device, a user input indicating the determined cut-off time of day.

7. The system of claim 1, wherein the supplemental sleep period is detected based at least in part on a first duration of the supplemental sleep period being less than a second duration of the primary sleep period.

8. The system of claim 1, wherein the set of one or more scores comprise a first score that is calculated using a set of factors, wherein, to update the set of one or more scores, the one or more processors are configured to:

update at least a subset of factors of the set of factors.

9. The system of claim 1, wherein the supplemental sleep period is detected based at least in part on a first duration of the supplemental sleep period being within a threshold range of durations.

10. The system of claim 1, wherein the one or more processors are further configured to:
generate a second signal to cause the GUI to display one or more insights associated with the user based at least in part on the primary sleep period and the supplemental sleep period, wherein the one or more insights comprise a suggestion associated with one or more characteristics of future supplemental sleep periods.

11. A method for supplemental sleep detection, comprising:
receiving, from a wearable device comprising one or more sensors, physiological data acquired from a user via the wearable device;
detecting a primary sleep period for the user during a sleep day based at least in part on a first subset of the physiological data, wherein the sleep day ends at a determined cut-off time of day;
generating a set of one or more scores associated with the sleep day based at least in part on the primary sleep period;
detecting a supplemental sleep period based at least in part on a second subset of the physiological data;
identifying a time of day that the supplemental sleep period occurred;
updating the set of one or more scores associated with the sleep day to generate an updated set of one or more scores based at least in part on the supplemental sleep period and based at least in part on the time of day associated with the supplemental sleep period occurring before the determined cut-off time of day;
generating one or more signals to cause a graphical user interface (GUI) of a user device associated with the wearable device to display the updated set of one or more scores after the supplemental sleep period and an indication of supplemental sleep period; and
receiving, via the user device and in response to the indication of the supplemental sleep period, a confirmation of the supplemental sleep period.

12. The method of claim 11, wherein the determined cut-off time of day is based at least in part on a time of day in which the user typically begins a primary sleep period each calendar day.

13. The method of claim 11, wherein the determined cut-off time of day is based at least in part on a sleeping pattern of the user.

14. The method of claim 11, wherein the determined cut-off time of day is associated with the user beginning a second primary sleep period associated with a second sleep day.

15. The method of claim 11, further comprising:
receiving, via the user device, a user input indicating the determined cut-off time of day.

16. The method of claim 11, wherein the supplemental sleep period is detected based at least in part on a first duration of the supplemental sleep period being less than a second duration of the primary sleep period.

17. The method of claim 16, wherein the set of one or more scores comprise a first score that is calculated using a set of factors, and wherein updating the set of one or more scores comprises:
updating at least a subset of factors of the set of factors.

18. The method of claim 11, further comprising:

generating a second signal to cause the GUI to display one or more insights associated with the user based at least in part on the primary sleep period and the supplemental sleep period, wherein the one or more insights comprise a suggestion associated with one or more characteristics of future supplemental sleep periods.

\* \* \* \* \*